(12) United States Patent
Comstock

(10) Patent No.: US 12,188,012 B2
(45) Date of Patent: Jan. 7, 2025

(54) COMPOSITIONS AND METHODS FOR MAKING CONTROLS FOR SEQUENCE-BASED GENETIC TESTING

(71) Applicant: Illumina, Inc., San Diego, CA (US)

(72) Inventor: David Comstock, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 474 days.

(21) Appl. No.: 16/372,622

(22) Filed: Apr. 2, 2019

(65) Prior Publication Data

US 2019/0367909 A1 Dec. 5, 2019

Related U.S. Application Data

(60) Provisional application No. 62/651,453, filed on Apr. 2, 2018.

(51) Int. Cl.
*C12N 15/10* (2006.01)

(52) U.S. Cl.
CPC ................ *C12N 15/1072* (2013.01)

(58) Field of Classification Search
CPC .......... C12N 15/1072; C12N 2525/191; C12Q 1/6855; C12Q 2525/191; C12Q 2600/166
See application file for complete search history.

(56) References Cited

U.S. PATENT DOCUMENTS

| | | | |
|---|---|---|---|
| 7,741,463 B2 | 6/2010 | Gormley et al. | |
| 8,053,192 B2 | 11/2011 | Bignell et al. | |
| 8,563,477 B2 | 10/2013 | Smith et al. | |
| 9,323,888 B2 | 4/2016 | Rava et al. | |
| 10,095,831 B2 | 10/2018 | Duenwald et al. | |
| 2005/0202490 A1 | 9/2005 | Makarov et al. | |
| 2007/0172839 A1 | 7/2007 | Smith et al. | |
| 2011/0201507 A1 | 8/2011 | Rava et al. | |
| 2012/0270739 A1 | 10/2012 | Rava et al. | |
| 2013/0029852 A1* | 1/2013 | Rava ............ | C12Q 1/6809 506/2 |
| 2013/0184796 A1 | 7/2013 | Marzano et al. | |
| 2014/0349891 A1 | 11/2014 | Liu et al. | |
| 2015/0368694 A1* | 12/2015 | Pan ............. | C12Q 1/6827 506/2 |

(Continued)

FOREIGN PATENT DOCUMENTS

| | | | |
|---|---|---|---|
| JP | 2014-223089 A | 12/2014 | |
| WO | WO-2005090607 A1 * | 9/2005 | ........... C12Q 1/6869 |
| WO | 2008096146 A1 | 8/2008 | |

(Continued)

OTHER PUBLICATIONS

Wilkie (CVR Bioinformatics, Jan. 26, 2015). (Year: 2015).*

(Continued)

*Primary Examiner* — Jeremy C Flinders
(74) *Attorney, Agent, or Firm* — Mueting Raasch Group

(57) ABSTRACT

Provided herein are compositions that include nucleic acid fragments produced from double-stranded template nucleic acids, such as cell free DNA. The compositions can be used as positive or negative controls for quality of library preparation methods, calibration of an instrument such as a sequencing instrument, and/or a validation for a nucleic acid sequencing test. Also provided are methods for making the nucleic acid fragments.

19 Claims, 4 Drawing Sheets

Specification includes a Sequence Listing.

(56) References Cited

U.S. PATENT DOCUMENTS

2018/0066306 A1* 3/2018 Namsaraev .......... C12Q 1/6816

FOREIGN PATENT DOCUMENTS

| WO | 2014014497 | 1/2014 | |
|---|---|---|---|
| WO | WO 2014/028778 A1 | 2/2014 | |
| WO | WO 2014/145078 A1 | 9/2014 | |
| WO | WO-2018140521 A1 * | 8/2018 | ............. G16B 20/00 |

OTHER PUBLICATIONS

International Search Report and Written Opinion for PCT/US2019/025304, issued by the European Patent Office, Jul. 17, 2019; 19 pgs.
Dey, "Integrated genome and transcriptome sequencing of the same cell," *Nature Biotechnology*, 2015;33:285-289.
Dey, "Integrated genome and transcriptome sequencing of the same cell," *Nature Biotechnology*, 2015;33:285-289; Supplementary Information.
Grisedale et al., "Linear amplification of target prior to PCR for improved low template DNA results," *Biotechniques*, Mar. 2014; 56:145-147.
Renaud et al., "leeHom: adaptor trimming and merging for Illumina sequencing reads," *Nucl Acids Res*, Aug. 6, 2014;42(18):e141-e141.
Salvi et al., "Cell-free DNA as a diagnostic marker for cancer: current insights," *OncoTargets and Therapy*, Oct. 25, 2016; 9:6549-6559.
Schubert et al., "Adapter Removal v2: rapid adapter trimming, identification, and read merging," *BMC Research Notes*, Feb. 12, 2016;9(1).
Sinauridze et al., "Moderate plasma dilution using artificial plasma expanders shifts the haemostatic balance to hypercoagulation," *Scientific Reports*, Apr. 12, 2017;7:843; 12 pgs.
Application of Everette L. May and Nathan B. Eddy, 574 F.2d 1082, 1090, 197 USPQ 601, 607 (CCPA 1978).

* cited by examiner

COMPOSITIONS AND METHODS FOR MAKING CONTROLS FOR SEQUENCE-BASED GENETIC TESTING

CROSS-REFERENCE TO RELATED APPLICATIONS

This application claims the benefit of U.S. Provisional Application Ser. No. 62/651,453, filed Apr. 2, 2018, which is incorporated by reference herein in its entirety.

SEQUENCE LISTING

This application contains a Sequence Listing electronically submitted via EFS-Web to the United States Patent and Trademark Office as an ASCII text file entitled "IP-1602-US_ST25.txt" having a size of 1.71 kilobytes and created on Jul. 22, 2019. The information contained in the Sequence Listing is incorporated by reference herein.

FIELD

The present disclosure relates to, among other things, making nucleic acid libraries that can be used as positive or negative controls and aid in validation of sequencing methods, and diagnostics for identifying over- and under-represented sequences in a library.

BACKGROUND

Prenatal screening and diagnosis are a routine part of antenatal care. Invasive tests exist for prenatal diagnosis of genetic and chromosomal conditions; however, amniocentesis or chorionic villus sampling have a risk of miscarriage of approximately 1%. Non-invasive tests based on the existence of circulating cell-free DNA in maternal blood use fetal nucleic acids from a maternal peripheral blood sample to determine fetal chromosomal abnormalities. Non-invasive methods offer an alternative and safer source of fetal genetic material for prenatal diagnosis.

Improvements in next-generation sequencing (NGS) technology have greatly increased sequencing speed and data output, resulting in the massive sample throughput of current sequencing platforms. The improvements have resulted in the rapid evolution of NGS in diagnostic techniques in the clinical laboratory. NGS technologies that allow for sequencing entire genomes in relatively short time have provided the opportunity to compare genetic material originating from one chromosome with that of another without the risks associated with invasive sampling methods.

Sequencing platforms of NGS technologies benefit from validation to confirm a platform will produce reliable results in the context of its intended use. Validation is aided by the use of positive and negative controls to include with each assay, qualify system installations, perform periodic performance qualifications, and qualify results for a clinical assay. Biological samples that can be used as negative controls are relatively abundant and easy to obtain. For instance, if a prenatal assay for Down's Syndrome is being run, a negative control can be a blood sample from a pregnant woman carrying a fetus that does not have Down's Syndrome. In contrast to negative controls, biological samples that can be used as positive controls are not readily available.

Synthetic positive controls that mimic biological samples are commercially available; however, they typically have one or more deficits. The DNA in synthetic positive controls that is intended to replace cell-free DNA is often uniform in size, while the cell-free DNA in a biological sample is not uniform in size. The DNA in synthetic positive controls often has uniform coverage of the genome used as a source of the DNA that is intended to replace cell-free DNA, but cell-free DNA in a biological sample does not necessarily have uniform coverage of the source's genome. Current approaches to yielding large quantities of DNA do not mimic the cell-free DNA fragment length, and even after processing, there are substantial deviations in both coverage and length. These deficits in synthetic positive controls have an effect on the statistical analysis of data from NGS technologies and introduce bias.

SUMMARY OF THE APPLICATION

Provided herein are methods for making and using collections of nucleic acid fragments, such as libraries, that can be used as positive or negative controls in many applications. In one embodiment, a method includes providing a sample that includes a plurality of double-stranded template nucleic acids obtained from a subject, and ligating a universal adaptor to both ends of the template nucleic acids to form a plurality of adaptor-template-adaptor molecules including a template nucleic acid flanked by the universal adaptor. In one embodiment, the universal adaptor includes a region of double stranded nucleic acid. The method can further include amplifying the plurality of adaptor-template-adaptor molecules with a first universal primer and a second universal primer to result in amplified adaptor-template-adaptor molecules, and removing at least a portion of the universal adaptor from both ends of the amplified adaptor-template-adaptor molecules to result in removed universal adaptors and a plurality of regenerated template nucleic acids (reDNAs). In one embodiment, the sample includes blood, urine, sputum, or stool.

In one embodiment, the subject is suspected of having a pathogen infection, such as an infection caused by a bacterial pathogen or a viral pathogen. In one embodiment, the sample includes viral DNA or bacterial DNA.

In one embodiment, the double-stranded template nucleic acids are DNA, and in some embodiments can include cell free DNA (cfDNA). In one embodiment, the subject is a pregnant human, and the double-stranded template nucleic acids include a mixture of fetal and maternal nucleic acids. In one embodiment, the fetus does not include a genetic condition, and in another embodiment the fetus includes a genetic condition. An example of a genetic condition is an aneuploidy, such as a trisomy. Examples of a trisomy include, but are not limited to, Trisomy 21, Trisomy 18, Trisomy 13, Trisomy 9, Trisomy 8, Trisomy 22, XXX, XXY, or XYY. In one embodiment, the genetic condition includes an under-representation of a nucleotide sequence. In another embodiment, a subject is suspected of having a neoplasm. In such a subject the sample can include circulating tumor DNA and cell free normal DNA.

In one embodiment, the method can further include treating, before the ligating, the plurality of double-stranded template nucleic acids to modify ends to be blunt ended. In one embodiment, the method can further include treating, before the ligating, the plurality of double-stranded template nucleic acids to modify 3' ends to terminate as a 3' overhang structure. The universal adaptor can further include a region of single-stranded non-complementary nucleic acid strands including at least one universal primer binding site, and wherein the ligating covalently attaches the region of double stranded nucleic acid of the universal adaptor to each end of the template nucleic acids.

In one embodiment, the amplifying includes an exponential amplification reaction, such as a polymerase chain reaction (PCR). In one embodiment, the amplifying includes a DNA polymerase with a low error rate.

In one embodiment the universal adaptor includes a restriction endonuclease recognition site, and the removing includes exposing the amplified adaptor-template-adaptor molecules to a restriction endonuclease and cleaving the adaptor-template-adaptor molecules to result in removed universal adaptors and a plurality of reDNAs. The cleavage site and the recognition site of the restriction endonuclease can be separate, and examples of useful restriction endonucleases include SapI, MlyI, or BpuEI. In one embodiment the reDNAs retain a portion of the universal adaptor at each end of the template, and in another embodiment the reDNAs do not retain a portion of the universal adaptor at each end of the template. In one embodiment, the first universal primer and the second universal primer include a capture agent, such as biotin.

In one embodiment where the universal adaptor includes a restriction endonuclease recognition site, the removing can include contacting the adaptor-template-adaptor molecules with a surface having a compound that binds a capture agent to result in bound amplified adaptor-template-adaptor molecules, and exposing the bound amplified adaptor-template-adaptor molecules to a restriction endonuclease that cleaves the bound amplified adaptor-template-adaptor molecules to result in removed universal adaptors and a plurality of reDNAs, where the removed universal adaptors are bound to the surface. In another embodiment, the separating can include contacting a mixture that includes the removed universal adaptors and the reDNAs with a compound that binds a capture agent, where the compound is attached to a surface, and where the removed universal adaptors are bound to the surface. An example of a surface is a bead. The method can further include removing the surface having the bound removed universal adaptors to result in separation of the removed universal adaptors from the reDNAs. The removing can further include selection of reDNAs that fall within a predetermined size range.

In one embodiment, a method includes providing a plurality of reDNAs originating from a sample obtained from a subject, where each reDNA is a template. The method can include ligating a universal adaptor to both ends of the template nucleic acids to form a plurality of adaptor-template-adaptor molecules including a template nucleic acid flanked by the universal adaptor. In one embodiment, the universal adapter includes (i) a region of double stranded nucleic acid, and (ii) a region of single-stranded non-complementary nucleic acid strands including at least one universal primer binding site, resulting in a sequencing library for determining the sequence of at least a portion of templates.

In one embodiment, the region of single-stranded non-complementary nucleic acid strands further includes at least one universal extension primer binding site. In one embodiment, the region of double stranded nucleic acid distal to the region of single-stranded non-complementary nucleic acid strands terminates as a blunt end structure. In one embodiment, the plurality of templates include blunt end structures. In one embodiment, the region of double stranded nucleic acid distal to the region of single-stranded non-complementary nucleic acid strands terminates as a 3' overhang structure. In one embodiment, the 3' overhang structure includes an overhang structure of, for instance, 1 to 4 nucleotides. In one embodiment, the 3' overhang structure includes an overhang of a T nucleotide. In one embodiment, the templates include a 3' overhang structure complementary to the 3' overhang structure of the region of double stranded nucleic acid.

The method can further include providing a surface including a plurality of amplification sites, where the amplification sites include at least two populations of attached single stranded nuclei acids having a free 3' end, and contacting the surface having amplification sites with the plurality of adaptor-template-adaptor molecules under conditions suitable to produce a plurality of amplification sites that each include a clonal population of amplicons from an individual adaptor-template-adaptor molecule. In one embodiment, the number of the plurality of adaptor-template-adaptor molecules exceeds the number of amplification sites, wherein the adaptor-template-adaptor molecules have fluidic access to the amplification sites, and wherein each of the amplification sites includes a capacity for several adaptor-template-adaptor molecules. In one embodiment, the contacting includes simultaneously (i) transporting the adaptor-template-adaptor molecules to the amplification sites at an average transport rate, and (ii) amplifying the adaptor-template-adaptor molecules that are at the amplification sites at an average amplification rate, wherein the average amplification rate exceeds the average transport rate.

Also provided herein are compositions. In one embodiment, a composition includes the adaptor-template-adaptor molecules described herein, where the universal adaptor includes a restriction endonuclease recognition site, such as SapI, MlyI, or BpuEI. In one embodiment, a composition includes the plurality of reDNAs generated by a method described herein and further including an artificial biological fluid. In one embodiment, the artificial biological fluid includes an artificial plasma.

Further provided herein is a method of using a control in a nucleic acid detection test. The method can include providing a plurality of reDNAs described herein, performing a nucleic acid detection test on a test sample and on the reDNAs, and analyzing results from the nucleic acid detection test using the reDNAs as a control. The nucleic acid detection test can include, for instance, sequencing or microarray analysis. In one embodiment, the nucleic acid detection test includes an enzymatic process.

Also provided herein is a method that includes performing a nucleic acid detection test on a plurality of reDNAs obtained using method described herein. The reDNAs can be, for instance, (i) a control for quality of library preparation methods, (ii) a calibration control for a sequencing instrument, (iii) a calibration control for an array instrument, (iv) a validation control for a nucleic acid sequencing test, such as for a sequencing-based noninvasive prenatal test or a sequencing-based tumor detection test, or (v) a validation control for a sequencing-based companion diagnostic test. In one embodiment, a companion diagnostic test can be used to determine the presence or identity of genetic variants and/or sequences of interest in a sample in order to determine whether a therapeutic treatment will be suitable in a treatment regimen.

Terms used herein will be understood to take on their ordinary meaning in the relevant art unless specified otherwise. Several terms used herein and their meanings are set forth below.

As used herein, the term "nucleic acid" is intended to be consistent with its use in the art and includes naturally occurring nucleic acids or functional analogs thereof. Particularly useful functional analogs are capable of hybridizing to a nucleic acid in a sequence specific fashion or capable of being used as a template for replication of a particular nucleotide sequence. Naturally occurring nucleic acids generally have a backbone containing phosphodiester bonds. An analog structure can have an alternate backbone linkage including any of a variety of those known in the art. Naturally occurring nucleic acids generally have a deoxyribose sugar (e.g. found in deoxyribonucleic acid (DNA)) or a ribose sugar (e.g. found in ribonucleic acid (RNA)). A nucleic acid can contain any of a variety of analogs of these sugar moieties that are known in the art. A nucleic acid can include native or non-native bases. In this regard, a native deoxyribonucleic acid can have one or more bases selected from the group consisting of adenine, thymine, cytosine or guanine and a ribonucleic acid can have one or more bases selected from the group consisting of uracil, adenine, cytosine or guanine. Useful non-native bases that can be included in a nucleic acid are known in the art. The term "template" and "target," when used in reference to a nucleic acid, is intended as a semantic identifier for the nucleic acid in the context of a method or composition set forth herein and does not necessarily limit the structure or function of the nucleic acid beyond what is otherwise explicitly indicated.

As used herein, the terms "template fragment" and related terms (e.g., "template nucleic acid fragment, "template molecule," and "template nucleic acid molecule") are used interchangeably to refer to nucleic acid molecules that it is desired ultimately to sequence, such as on an array, or to use to produce a composition.

As used herein, the term "adaptor" and its derivatives, e.g., universal adaptor, refers generally to any linear oligonucleotide which can be ligated to a nucleic acid molecule described herein. In some embodiments, the adapter is substantially non-complementary to the 3' end or the 5' end of any template sequence present in the sample. In some embodiments, suitable adapter lengths are in the range of about 10-100 nucleotides, about 12-60 nucleotides and about 15-50 nucleotides in length. Generally, the adapter can include any combination of nucleotides and/or nucleic acids. In some embodiments, the adapter can include one or more cleavable groups at one or more locations. In some embodiments, the adapter can include one or more universal sequences. In another embodiment, the adapter can include a sequence that is substantially identical, or substantially complementary, to at least a portion of a primer, for example a universal primer. In some embodiments, the adapter can include an index, also referred to herein as a barcode, to assist with downstream error correction, identification or sequencing. The terms "adaptor" and "adapter" are used interchangeably.

As used herein, the term "universal sequence" refers to a region of sequence that is common to two or more nucleic acid molecules, e.g., adaptor-template-adaptor molecules, where the molecules also have regions of sequence that differ from each other. A universal sequence that is present in different members of a collection of molecules can allow capture of multiple different nucleic acids using a population of universal capture nucleic acids that are complementary to a portion of the universal sequence, e.g., a universal extension primer binding site. Non-limiting examples of universal extension primer binding sites include sequences that are identical to or complementary to P5 and P7 primers. Similarly, a universal sequence present in different members of a collection of molecules can allow the replication or amplification of multiple different nucleic acids using a population of universal primers that are complementary to a portion of the universal sequence, e.g., a universal primer binding site. Thus a universal capture nucleic acid or a universal primer includes a sequence that can hybridize specifically to a universal sequence. Template nucleic acid molecules may be modified to attach universal adaptors (also referred to herein as adaptors), for example, at one or both ends of the different template sequences, as described herein. In another embodiment, a universal sequence that is present in different members of a collection of molecules can allow for removal of a portion of the universal adaptor from the template molecule to which it is attached, e.g., a universal removal sequence.

The terms "P5" and "P7" may be used when referring to amplification primers, e.g., universal primer extension primers. The terms "P5'" (P5 prime) and "P7'" (P7 prime) refer to the complement of P5 and P7, respectively. It will be understood that any suitable amplification primers can be used in the methods presented herein, and that the use of P5 and P7 are exemplary embodiments only. Uses of amplification primers such as P5 and P7 on flowcells is known in the art, as exemplified by the disclosures of WO 2007/010251, WO 2006/064199, WO 2005/065814, WO 2015/106941, WO 1998/044151, and WO 2000/018957. For example, any suitable forward amplification primer, whether immobilized or in solution, can be useful in the methods presented herein for hybridization to a complementary sequence and amplification of a sequence. Similarly, any suitable reverse amplification primer, whether immobilized or in solution, can be useful in the methods presented herein for hybridization to a complementary sequence and amplification of a sequence. One of skill in the art will understand how to design and use primer sequences that are suitable for capture, and amplification of nucleic acids as presented herein.

As used herein, "amplify," "amplifying" or "amplification reaction" and their derivatives, refer generally to any action or process whereby at least a portion of a nucleic acid molecule is replicated or copied into at least one additional nucleic acid molecule. The additional nucleic acid molecule optionally includes sequence that is substantially identical or substantially complementary to at least some portion of the target nucleic acid molecule. The target nucleic acid molecule can be single-stranded or double-stranded and the additional nucleic acid molecule can independently be single-stranded or double-stranded. Amplification optionally includes linear or exponential replication of a nucleic acid molecule. In some embodiments, such amplification can be performed using isothermal conditions; in other embodiments, such amplification can include thermocycling. In some embodiments, the amplification is a multiplex amplification that includes the simultaneous amplification of a plurality of target sequences in a single amplification reaction. In some embodiments, "amplification" includes amplification of at least some portion of DNA and RNA based nucleic acids alone, or in combination. The amplification reaction can include any of the amplification processes known to one of ordinary skill in the art. In some embodiments, the amplification reaction includes polymerase chain reaction (PCR).

As used herein, "amplification conditions" and its derivatives, generally refers to conditions suitable for amplifying one or more nucleic acid sequences. Such amplification can be linear or exponential. In some embodiments, the amplification conditions can include isothermal conditions or alternatively can include thermocycling conditions, or a combination of isothermal and thermocycling conditions. In some embodiments, the conditions suitable for amplifying one or more nucleic acid sequences include polymerase chain reaction (PCR) conditions. Typically, the amplification conditions refer to a reaction mixture that is sufficient to amplify nucleic acids such as one or more target sequences, or to amplify an amplified target sequence ligated to one or more adapters, e.g., an adapter-ligated amplified target sequence. Generally, the amplification conditions include a catalyst for amplification or for nucleic acid synthesis, for example a polymerase; a primer that possesses some degree of complementarity to the nucleic acid to be amplified; and nucleotides, such as deoxyribonucleotide triphosphates (dNTPs) to promote extension of the primer once hybridized to the nucleic acid. The amplification conditions can require hybridization or annealing of a primer to a nucleic acid, extension of the primer and a denaturing step in which the extended primer is separated from the nucleic acid sequence undergoing amplification. Typically, but not necessarily, amplification conditions can include thermocycling; in some embodiments, amplification conditions include a plurality of cycles where the steps of annealing, extending and separating are repeated. Typically, the amplification conditions include cations such as $Mg^{++}$ or $Mn^{++}$ and can also include various modifiers of ionic strength.

As used herein, "reamplification" and its derivatives refer generally to any process whereby at least a portion of an amplified nucleic acid molecule is further amplified via any suitable amplification process (referred to in some embodiments as a "secondary" amplification), thereby producing a reamplified nucleic acid molecule. The secondary amplification need not be identical to the original amplification process whereby the amplified nucleic acid molecule was produced; nor need the reamplified nucleic acid molecule be completely identical or completely complementary to the amplified nucleic acid molecule; all that is required is that the reamplified nucleic acid molecule include at least a portion of the amplified nucleic acid molecule or its complement. For example, the reamplification can involve the use of different amplification conditions and/or different primers, including different target-specific primers than the primary amplification.

As used herein, the term "polymerase chain reaction" ("PCR") refers to the method of K. B. Mullis U.S. Pat. Nos. 4,683,195 and 4,683,202, which describe a method for increasing the concentration of a segment of a polynucleotide of interest in a mixture of genomic DNA without cloning or purification. This process for amplifying the polynucleotide of interest consists of introducing a large excess of two oligonucleotide primers to the DNA mixture containing the desired polynucleotide of interest, followed by a series of thermal cycling in the presence of a DNA polymerase. The two primers are complementary to their respective strands of the double-stranded polynucleotide of interest. The mixture is denatured at a higher temperature first and the primers are then annealed to complementary sequences within the polynucleotide of interest molecule. Following annealing, the primers are extended with a polymerase to form a new pair of complementary strands. The steps of denaturation, primer annealing and polymerase extension can be repeated many times (referred to as thermocycling) to obtain a high concentration of an amplified segment of the desired polynucleotide of interest. The length of the amplified segment of the desired polynucleotide of interest (amplicon) is determined by the relative positions of the primers with respect to each other, and therefore, this length is a controllable parameter. By virtue of repeating the process, the method is referred to as the "polymerase chain reaction" (hereinafter "PCR"). Because the desired amplified segments of the polynucleotide of interest become the predominant nucleic acid sequences (in terms of concentration) in the mixture, they are said to be "PCR amplified". In a modification to the method discussed above, the target nucleic acid molecules can be PCR amplified using a plurality of different primer pairs, in some cases, one or more primer pairs per target nucleic acid molecule of interest, thereby forming a multiplex PCR reaction.

As defined herein "multiplex amplification" refers to selective and non-random amplification of two or more target sequences within a sample using at least one target-specific primer. In some embodiments, multiplex amplification is performed such that some or all of the target sequences are amplified within a single reaction vessel. The "plexy" or "plex" of a given multiplex amplification refers generally to the number of different target-specific sequences that are amplified during that single multiplex amplification. In some embodiments, the plexy can be about 12-plex, 24-plex, 48-plex, 96-plex, 192-plex, 384-plex, 768-plex, 1536-plex, 3072-plex, 6144-plex or higher. It is also possible to detect the amplified target sequences by several different methodologies (e.g., gel electrophoresis followed by densitometry, quantitation with a bioanalyzer or quantitative PCR, hybridization with a labeled probe; incorporation of biotinylated primers followed by avidin-enzyme conjugate detection; incorporation of 32P-labeled deoxynucleotide triphosphates into the amplified target sequence).

As used herein, the term "primer" and its derivatives refer generally to any polynucleotide that can hybridize to a target sequence of interest. Typically, the primer functions as a substrate onto which nucleotides can be polymerized by a polymerase; in some embodiments, however, the primer can become incorporated into the synthesized nucleic acid strand and provide a site to which another primer can hybridize to prime synthesis of a new strand that is complementary to the synthesized nucleic acid molecule. The primer can include any combination of nucleotides or analogs thereof. In some embodiments, the primer is a single-stranded oligonucleotide or polynucleotide. The terms "polynucleotide" and "oligonucleotide" are used interchangeably herein to refer to a polymeric form of nucleotides of any length, and may comprise ribonucleotides, deoxyribonucleotides, analogs thereof, or mixtures thereof. The terms should be understood to include, as equivalents, analogs of either DNA, such as cell free DNA (cfDNA), or RNA made from nucleotide analogs and to be applicable to single stranded (such as sense or antisense) and double-stranded polynucleotides. The term as used herein also encompasses cDNA, that is complementary or copy DNA produced from a RNA template, for example by the action of reverse transcriptase. This term refers only to the primary structure of the molecule. Thus, the term includes triple-, double- and single-stranded deoxyribonucleic acid ("DNA"), as well as triple-, double- and single-stranded ribonucleic acid ("RNA").

As used herein, a "cell free DNA" ("cfDNA") and cell free circulating DNA ("cffDNA") are used interchangeably and refer to DNA that, when it is present in subject, is not associated with a cell. cfDNA can originate from various sources of a subject, including, but not limited to, a biological fluid such as blood, plasma, serum, urine and saliva.

As used herein, the term "subject" refers to a human subject as well as a non-human subject such as a mammal. Although the examples herein concern humans and the language is primarily directed to human concerns, the concept of this disclosure is applicable to genomes from any animal, and is useful in the fields of veterinary medicine, animal sciences, research laboratories and such.

As defined herein, "sample" and its derivatives, is used in its broadest sense and includes any specimen, culture and the like that is suspected of including a template useful in the methods described herein. The sample can include any biological (e.g., clinical or surgical) sample containing one or more nucleic acids. In one embodiment, the sample is the result of a "liquid biopsy," e.g., a biological fluid such as blood, plasma, serum, urine, saliva, sputum, lavage fluid, cerebrospinal fluid, semen, sweat, tears, saliva, stool, and the like. As used herein, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

The term "maternal sample" herein refers to a biological sample obtained from a pregnant subject.

As used herein, the terms "library" and "sequencing library" refer to a collection or plurality of template molecules which share common sequences at their 5' ends and common sequences at their 3' ends. The collection of template molecules containing known common sequences at their 3' and 5' ends may also be referred to as a 3' and 5' modified library.

The term "sequence of interest" herein refers to a nucleic acid sequence that is associated with a difference in sequence representation in healthy individuals versus an individual having a condition described herein, e.g., a genetic condition or a neoplasm. A sequence of interest can be a sequence on a chromosome that is misrepresented, i.e., over- or under-represented (including deleted), in a condition. A sequence of interest can be a sequence that is known or suspected to play a role in the development and/or progression of a condition. A sequence of interest may also be a portion of a chromosome, or a chromosome. For example, a sequence of interest can be a chromosome or portion thereof that is over-represented in an aneuploidy condition, or a gene or portion thereof encoding a tumor-suppressor that is under-represented in a cancer. A sequence of interest may be a portion of a pathogen genome, for example a viral or microbial genome. A sequence of interest may be a genetic variant, such as a single nucleotide polymorphism.

The term "aneuploidy" herein refers to an imbalance of genetic material caused by a loss or gain of a whole chromosome, or part of a chromosome.

The term "chromosomal aneuploidy" herein refers to an imbalance of genetic material caused by a loss or gain of a whole chromosome, and includes germline aneuploidy and mosaic aneuploidy.

The term "partial aneuploidy" herein refers to an imbalance of genetic material caused by a loss or gain of part of a chromosome e.g. partial monosomy and partial trisomy, and encompasses imbalances resulting from translocations, deletions, and insertions.

The term "neoplasm" as used herein refers to an abnormal growth of tissue, which if it forms a mass, is typically referred to as a tumor. A neoplasm can be malignant (a cancer) or benign (not a cancer).

As used herein, "amplified adaptor-template-adaptor molecules" and its derivatives, refers generally to a nucleic acid sequence produced by the amplifying adaptor-template-adaptor sequences using target-specific primers and the methods provided herein. The amplified adaptor-template-adaptor sequences may be either of the same sense (i.e., the positive strand) or antisense (i.e., the negative strand) with respect to the template sequences.

As used herein, the terms "ligating," "ligation" and their derivatives refer generally to the process for covalently linking two or more molecules together, for example covalently linking two or more nucleic acid molecules to each other. In some embodiments, ligation includes joining nicks between adjacent nucleotides of nucleic acids. In some embodiments, ligation includes forming a covalent bond between an end of a first and an end of a second nucleic acid molecule. In some embodiments, the ligation can include forming a covalent bond between a 5' phosphate group of one nucleic acid and a 3' hydroxyl group of a second nucleic acid thereby forming a ligated nucleic acid molecule. Generally, for the purposes of this disclosure, an amplified target sequence can be ligated to an adapter to generate an adapter-ligated amplified target sequence.

As used herein, the terms "blunt-ending" and "end-repairing" interchangeably refer to an enzymatic process that results in both strands of a double-stranded DNA molecule to terminate in a base pair, and does not include purifying the blunt-ended products from the blunt-ending enzyme.

As used herein, the term "tailing" refers to an enzymatic process that adds at least one nucleotide, typically an adenine, to the 3' end of DNA, and does not include purifying the tailed product from the tailing enzyme.

As used herein, "ligase" and its derivatives, refers generally to any agent capable of catalyzing the ligation of two substrate molecules. In some embodiments, the ligase includes an enzyme capable of catalyzing the joining of nicks between adjacent nucleotides of a nucleic acid. In some embodiments, the ligase includes an enzyme capable of catalyzing the formation of a covalent bond between a 5' phosphate of one nucleic acid molecule to a 3' hydroxyl of another nucleic acid molecule thereby forming a ligated nucleic acid molecule. Suitable ligases may include, but not limited to, T4 DNA ligase, T4 RNA ligase, and *E. coli* DNA ligase.

As used herein, "ligation conditions" and its derivatives, generally refers to conditions suitable for ligating two molecules to each other. In some embodiments, the ligation conditions are suitable for sealing nicks or gaps between nucleic acids. As used herein, the term nick or gap is consistent with the use of the term in the art. Typically, a nick or gap can be ligated in the presence of an enzyme, such as ligase at an appropriate temperature and pH. In some embodiments, T4 DNA ligase can join a nick between nucleic acids at a temperature of about 70-72° C.

The term "flowcell" as used herein refers to a chamber comprising a solid surface across which one or more fluid reagents can be flowed. Examples of flowcells and related fluidic systems and detection platforms that can be readily used in the methods of the present disclosure are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082.

As used herein, the term "amplicon," when used in reference to a nucleic acid, means the product of copying the nucleic acid, wherein the product has a nucleotide sequence that is the same as or complementary to at least a portion of the nucleotide sequence of the nucleic acid. An amplicon can be produced by any of a variety of amplification methods that use the nucleic acid, or an amplicon thereof, as a template including, for example, PCR, rolling circle amplification (RCA), ligation extension, or ligation chain reaction. An amplicon can be a nucleic acid molecule having a single copy of a particular nucleotide sequence (e.g. a PCR product) or multiple copies of the nucleotide sequence (e.g. a concatameric product of RCA). A first amplicon of a target nucleic acid is typically a complementary copy. Subsequent amplicons are copies that are created, after generation of the first amplicon, from the target nucleic acid or from the first amplicon. A subsequent amplicon can have a sequence that is substantially complementary to the target nucleic acid or substantially identical to the target nucleic acid.

As used herein, the term "amplification site" refers to a site in or on an array where one or more amplicons can be generated. An amplification site can be further configured to contain, hold or attach at least one amplicon that is generated at the site.

As used herein, the term "array" refers to a population of sites that can be differentiated from each other according to relative location. Different molecules that are at different sites of an array can be differentiated from each other according to the locations of the sites in the array. An individual site of an array can include one or more molecules of a particular type. For example, a site can include a single target nucleic acid molecule having a particular sequence or a site can include several nucleic acid molecules having the same sequence (and/or complementary sequence, thereof). The sites of an array can be different features located on the same substrate. Exemplary features include without limitation, wells in a substrate, beads (or other particles) in or on a substrate, projections from a substrate, ridges on a substrate or channels in a substrate. The sites of an array can be separate substrates each bearing a different molecule. Different molecules attached to separate substrates can be identified according to the locations of the substrates on a surface to which the substrates are associated or according to the locations of the substrates in a liquid or gel. Exemplary arrays in which separate substrates are located on a surface include, without limitation, those having beads in wells.

As used herein, the term "capacity," when used in reference to a site and nucleic acid material, means the maximum amount of nucleic acid material that can occupy the site. For example, the term can refer to the total number of nucleic acid molecules that can occupy the site in a particular condition. Other measures can be used as well including, for example, the total mass of nucleic acid material or the total number of copies of a particular nucleotide sequence that can occupy the site in a particular condition. Typically, the capacity of a site for a target nucleic acid will be substantially equivalent to the capacity of the site for amplicons of the target nucleic acid.

As used herein, the term "capture agent" refers to a material, chemical, molecule or moiety thereof that is capable of attaching, retaining or binding to a target molecule (e.g. a target nucleic acid). Exemplary capture agents include, without limitation, a capture nucleic acid that is complementary to at least a portion of a target nucleic acid, a member of a receptor-ligand binding pair (e.g. avidin, streptavidin, biotin, lectin, carbohydrate, nucleic acid binding protein, epitope, antibody, etc.) capable of binding to a target nucleic acid (or linking moiety attached thereto), or a chemical reagent capable of forming a covalent bond with a target nucleic acid (or linking moiety attached thereto).

As used herein, the term "clonal population" refers to a population of nucleic acids that is homogeneous with respect to a particular nucleotide sequence. The homogenous sequence is typically at least 10 nucleotides long, but can be even longer including for example, at least 50, 100, 250, 500 or 1000 nucleotides long. A clonal population can be derived from a single target nucleic acid or template nucleic acid. Typically, all of the nucleic acids in a clonal population will have the same nucleotide sequence. It will be understood that a small number of mutations (e.g. due to amplification artifacts) can occur in a clonal population without departing from clonality.

As used herein, the term "transport" refers to movement of a molecule through a fluid. The term can include passive transport such as movement of molecules along their concentration gradient (e.g. passive diffusion). The term can also include active transport whereby molecules can move along their concentration gradient or against their concentration gradient. Thus, transport can include applying energy to move one or more molecule in a desired direction or to a desired location such as an amplification site.

As used herein, the term "each," when used in reference to a collection of items, is intended to identify an individual item in the collection but does not necessarily refer to every item in the collection unless the context clearly dictates otherwise.

As used herein, "providing" in the context of a composition, an article, a nucleic acid, or a nucleus means making the composition, article, nucleic acid, or nucleus, purchasing the composition, article, nucleic acid, or nucleus, or otherwise obtaining the compound, composition, article, or nucleus.

The term "and/or" means one or all of the listed elements or a combination of any two or more of the listed elements.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

The terms "comprises" and variations thereof do not have a limiting meaning where these terms appear in the description and claims.

It is understood that wherever embodiments are described herein with the language "include," "includes," or "including," and the like, otherwise analogous embodiments described in terms of "consisting of" and/or "consisting essentially of" are also provided.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments.

For any method disclosed herein that includes discrete steps, the steps may be conducted in any feasible order. And, as appropriate, any combination of two or more steps may be conducted simultaneously.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

The following detailed description of illustrative embodiments of the present disclosure may be best understood when read in conjunction with the following drawings.

The schematic drawings are not necessarily to scale. Like numbers used in the figures may refer to like components. However, it will be understood that the use of a number to refer to a component in a given figure is not intended to limit the component in another figure labeled with the same number. In addition, the use of different numbers to refer to components is not intended to indicate that the different numbered components cannot be the same or similar to other numbered components.

DETAILED DESCRIPTION OF ILLUSTRATIVE EMBODIMENTS

Figure 1:
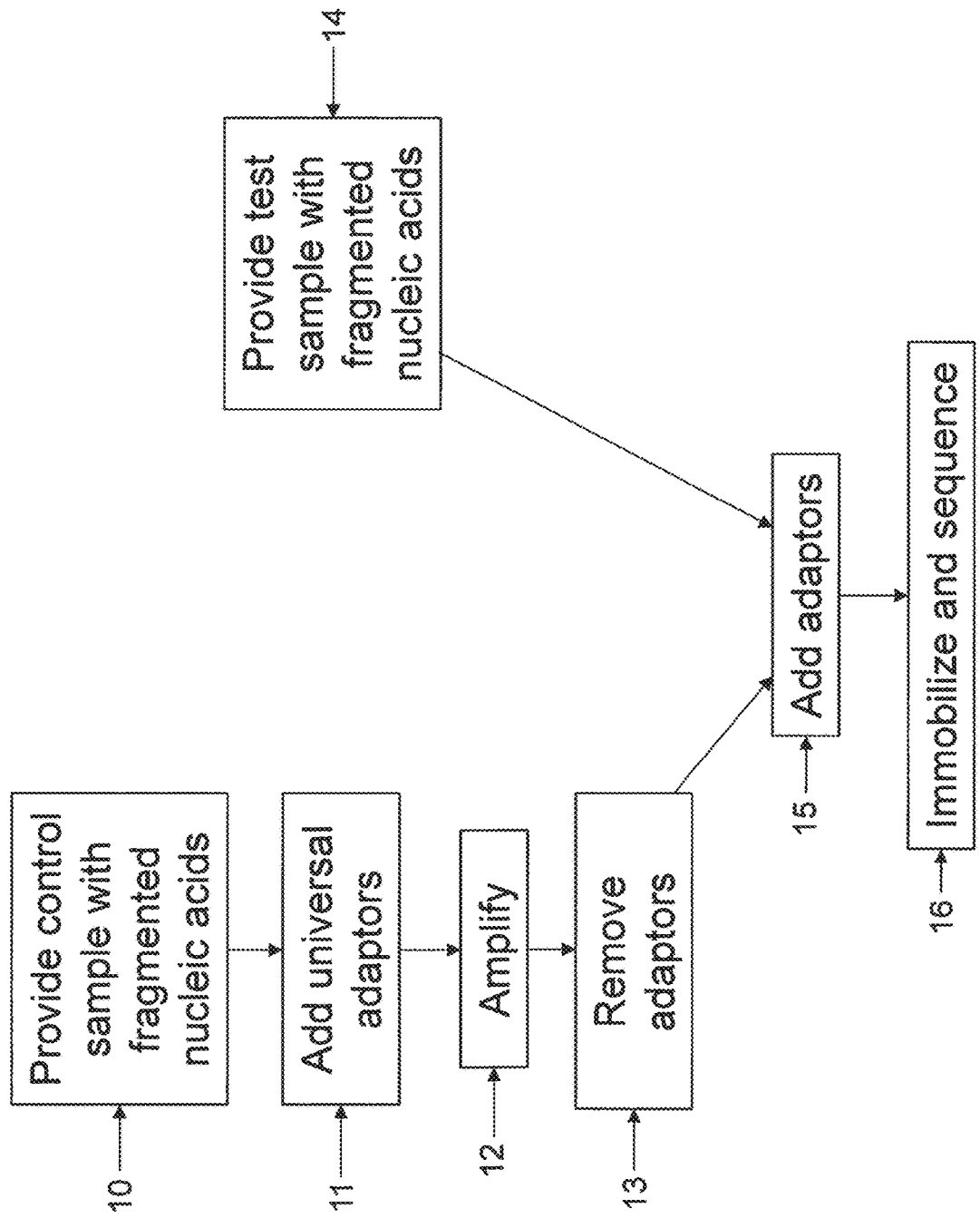
FIG. 1 shows a general block diagram of a general illustrative method according to the present disclosure.
Figure 2:
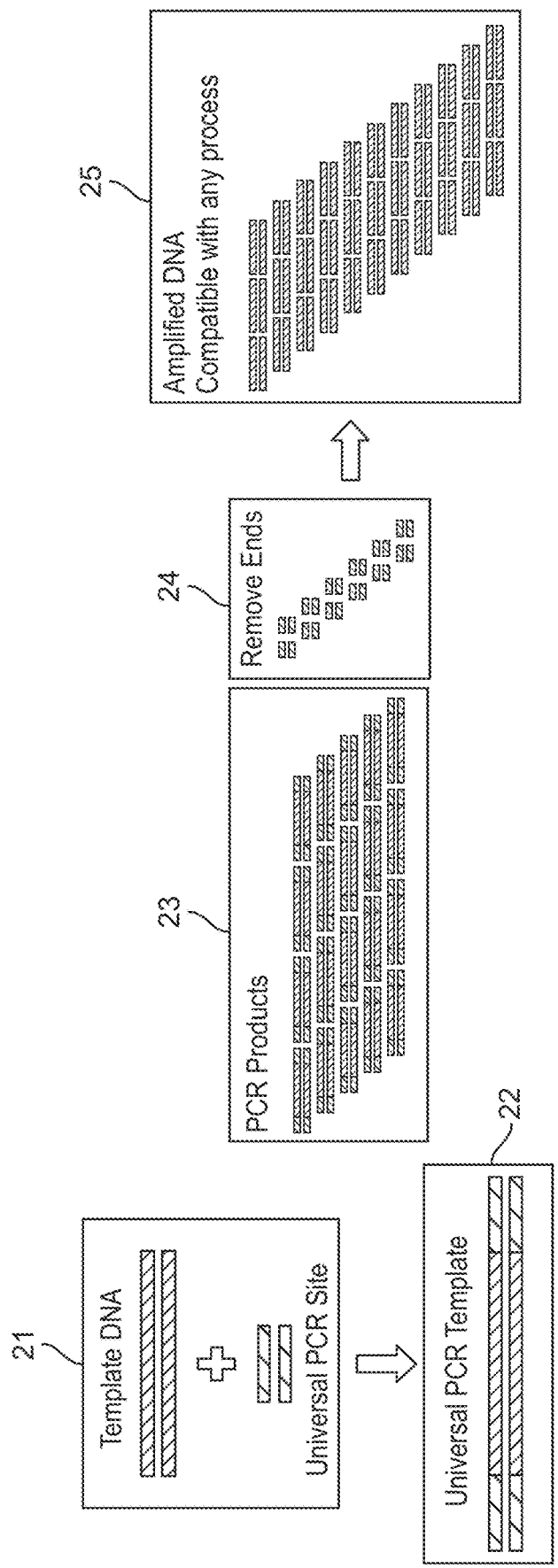
FIG. 2 shows a more detailed diagram of one embodiment for adding universal adaptors, amplifying, and removing adaptors generally illustrated in the method of FIG. 1.

Provided herein are methods for making libraries that can be used as positive or negative controls to determine reproducibility, qualify system installations, perform periodic performance qualifications, qualify results for a clinical assay, and the like. In one embodiment, the method includes providing a control sample that includes fragmented nucleic acids (FIG. 1, block 10) that can be used as templates, and adding universal adaptors to each end of the nucleic acid fragments (FIG. 1, block 11; FIG. 2, block 21). The result of the added universal adaptors is shown in FIG. 2, block 22. The fragments that are flanked by the adaptors are amplified (FIG. 1, block 12) to result in amplification products, e.g., PCR products (FIG. 2, block 23); however, in contrast to methods directed to determining the sequence of fragments in a library, the adaptors are subsequently removed (FIG. 1, block 13; FIG. 2, block 24). The result is an amplified library of nucleic acids that includes the fragmented nucleic acids originally present in the control sample (FIG. 2, block 25). This population of amplified fragments is also referred to herein interchangeably as regenerated template nucleic acids, regenerated DNA, or reDNA. This amplified library can be used as a control in standard methods for determining, for example, whether a test sample includes an aneuploidy. For instance, a test sample that is to be assayed for the presence or absence of an aneuploidy can be obtained (FIG. 1, block 14) and prepared for sequencing, such as having adaptors added (FIG. 1, block 15). In the same method the control can also have adaptors added (FIG. 1, block 15) and both the test and control samples processed for immobilization and sequencing (FIG. 1, block 16). The reDNA fragments, for instance a reDNA library, resulting from the removal of adaptors (FIG. 1, block 13) provides many advantages including a population of fragments of sizes similar to or identical to the sizes observed in the original biological sample, and genomic coverage that is similar to or identical to the original biological sample. Further advantageous is that, unlike other processing methods that may leave adapters (or portions thereof) attached to the ends of the fragments, methods presented herein do not leave behind any fragments of adaptors or side products of processes used to amplify the material.

The libraries provided herein can be used to determine copy number variations (CNV) of any sequence of interest in a sample (a control sample or a test sample) that includes a mixture of templates that are known or are suspected to differ in the amount of one or more sequence of interest. Sequences of interest include genomic sequences ranging from tens of bases, to hundreds of bases, to tens of megabases, and to entire chromosomes that are known or are suspected to be associated with a condition.

In one embodiment, the method includes providing one or more of a plurality of double-stranded template nucleic acids, e.g., a control sample (FIG. 1, block 10), reDNA (the result of adaptor removal, FIG. 1, block 13), or a test sample (FIG. 1, block 14). The template nucleic acid may be essentially any nucleic acid of known or unknown sequence. It may be, for example, a fragment of genomic DNA. In one embodiment, the template nucleic acid is a cell free DNA (cfDNA). In one embodiment, the templates can be derived from a biological sample. In one embodiment, the templates can be processed so they are suitable for amplification by the placement of a universal sequence, e.g., sequences present in a universal adaptor, at the ends of each template fragment. In one embodiment, the template fragments can also be processed to have the sequence determined, where sequencing may result in determination of the sequence of the whole, or a part of the template. The templates can also be obtained from a RNA sample by reverse transcription into cDNA.

The templates may originate in double-stranded DNA (dsDNA) form (e.g. genomic DNA fragments, cfDNAs, PCR and amplification products, and the like) from a sample or may have originated in single-stranded form from a sample, as DNA or RNA, and been converted to dsDNA form. In some embodiments, such as embodiments where the templates will be used as a control (e.g., FIG. 1, block 10), the sequence of the polynucleotide molecules from a nucleic acid sample may be known. In other embodiments, such as embodiments where the templates are from a test sample, the sequence of the polynucleotide molecules from a nucleic acid sample may not be known (e.g., FIG. 1, block 14).

In one embodiment, the templates from a sample are RNA molecules. In an aspect of this embodiment, RNA isolated from a sample is first converted to double-stranded DNA using techniques known in the art.

In one embodiment, the templates from a sample are DNA molecules. In one embodiment, the templates represent the entire genetic complement of an organism, and are genomic DNA molecules which include both intron and exon sequences, as well as non-coding regulatory sequences such as promoter and enhancer sequences. In one embodiment, the templates represent particular sub-sets of polynucleotide sequences, such as, for example, a particular chromosome or a cfDNA. Still yet more particularly, the templates are human, such as human genomic DNA molecules, a human chromosome, or human cfDNA. The templates may be treated chemically or enzymatically either prior or subsequent to any random fragmentation processes, and prior or subsequent to the ligation of the universal adapter sequences.

In one embodiment, a sample can be from a single individual. An example of a single individual is a pregnant woman. The fetus being carried by the woman can be one that does or does not have a sequence of interest, e.g., a genetic condition. Methods for determining whether a fetus carried by a woman has a genetic condition can be determined using methods disclosed herein, and methods known to the skilled person including amniocentesis and sequencing methods (Lo et al., WO2009/013496; Quake et al., WO2007/092473; Rava et al., US Patent Publication 2012/0270739). Another example of a single individual is a person known to have or suspected of having a condition such as, but not limited to, a genetic condition, an inherited genetic disorder, a genetic mutation, a neoplasm, an autoimmune disease, or a transplantation. A sample from a single source can contain two or more distinct forms of genetic material, such as maternal and fetal nucleic acids obtained from a maternal subject, or normal and neoplasm nucleic acids obtained from a subject having, for instance, a neoplasm. Further, samples from a single source can contain multiple distinct forms of genetic material, such as a subject pregnant with twins, triplets, and the like, or a subject with multiple distinct neoplasms. In some embodiments, the multiple distinct forms of genetic material can be from the subject and an invasive organism such as a parasite, bacterial or viral infection, and the like.

In one embodiment, the sample can be for use as a control sample. A control sample is one that is processed to result in a population of reDNA fragments, for instance a reDNA library (e.g., the result of adaptor removal, FIG. 1, block 13) that can be used as a control. Methods for preparing a library from a sample are known (see, e.g., Gormley et al., U.S. Pat. No. 7,741,463; Rava et al., US Patent Publication 2012/0270739). Typically, the copy number variation of a sequence of interest in the amplified library is known, or is determined so that the sample can be used as a control. For instance, if the sample is from a pregnant woman the copy number variation of a sequence of interest of the fetus can be determined. If the fetus has a specific condition, such as an aneuploidy, the sample can be used as a positive control. Alternatively, if the fetus does not have an aneuploidy the sample can be used as a negative control. As described herein and shown schematically in FIG. 1 (see blocks 10-13), a control sample is processed to result in an amplified library.

In another embodiment, the sample is a test sample (e.g., FIG. 1, block 14). In one embodiment, a test sample is one that is processed to determine the sequence of a sufficient number of nucleotides to determine the copy number variation of a sequence of interest in the test sample. This can be indicative of a healthy individual or an individual having a genetic condition described herein. In one embodiment, a test sample is one that is processed to determine the sequence of a sufficient number of nucleotides to determine the presence of a pathogen sequence of interest, which can be indicative of, for instance, a viral or microbial infection. In one embodiment, a test sample is one that is processed to determine the sequence of a sufficient number of nucleotides to determine the presence of one or more genetic variants or sequences of interest, such as a single nucleotide polymorphism (SNP), an insertion, deletion, rearrangement, or a specific mutation of an allele. The identification of the genetic variant (e.g., SNP or mutation) can be used as a companion diagnostic test to determine the applicability of a therapy to a specific individual.

Examples of a sequence of interest includes a genetic condition such as, but not limited to, an aneuploidy. In some embodiments, the aneuploidy is a complete chromosomal trisomy or monosomy, or a partial trisomy or monosomy. Partial aneuploidies are caused by loss or gain of part of a chromosome, and encompass chromosomal imbalances resulting from unbalanced translocations, unbalanced inversions, deletions and insertions. The most common known aneuploidy compatible with life is trisomy 21, i.e., Down Syndrome (DS), which is caused by the presence of part or all of chromosome 21. Rarely, DS can be caused by an inherited or sporadic defect whereby an extra copy of all or part of chromosome 21 becomes attached to another chromosome (usually chromosome 14) to form a single aberrant chromosome. DS is associated with intellectual impairment, severe learning difficulties and excess mortality caused by long-term health problems such as heart disease. Other aneuploidies with known clinical significance include Edward syndrome (trisomy 1S) and Patau Syndrome (trisomy 13), which are frequently fatal within the first few months of life. Abnormalities associated with the number of sex chromosomes are also known and include monosomy X, e.g., Turner syndrome (XO), and triple X syndrome (XXX) in female births and Kleinefelter syndrome (XXY) and XYY syndrome in male births, which are all associated with various phenotypes including sterility and reduction in intellectual skills.

A trisomy can be trisomy 21 (T21; Down Syndrome), trisomy 1S (TIS; Edward's Syndrome), trisomy 16 (T16), trisomy 22 (T22; Cat Eye Syndrome), trisomy 15 (T15; Prader Willi Syndrome), trisomy 13 (T13; Patau Syndrome), trisomy S (TS; Warkany Syndrome) and the XXY (Kleinefelter Syndrome), XYY, or XXX trisomies. It will be appreciated that various other trisomies and partial trisomies can be present in a sample from a single individual. These include, but not limited to, partial trisomy 1 q32-44, trisomy 9 p with trisomy, trisomy 4 mosaicism, trisomy 17p, partial trisomy 4q26-qter, trisomy 9, partial 2p trisomy, partial trisomy 1q, and/or partial trisomy 6p/monosomy 6q.

Other genetic conditions that can be present in a sample from a single individual include, but are not limited to, chromosomal monosomy X, and partial monosomies such as, monosomy 13, monosomy 15, monosomy 16, monosomy 21, and monosomy 22, which are known to be involved in pregnancy miscarriage. Monosomy 1 Sp is a rare chromosomal disorder in which all or part of the short arm (p) of chromosome 1 S is deleted (monosomic). The disorder is typically characterized by short stature, variable degrees of mental retardation, speech delays, malformations of the skull and facial (craniofacial) region, and/or additional physical abnormalities. Associated craniofacial defects may vary greatly in range and severity from case to case. Conditions caused by changes in the structure or number of copies of chromosome 15 include Angelman Syndrome and Prader-Willi Syndrome, which involve a loss of gene activity in the same part of chromosome 15, the 15q 11-q 13 region. It will be appreciated that several translocations and microdeletions can be asymptomatic in the carrier parent, yet can cause a major genetic disease in the offspring. For example, a healthy mother who carries the 15q 11-q 13 microdeletion can give birth to a child with Angelman syndrome, a severe neurodegenerative disorder. Thus, the present disclosure can be used to identify such a deletion in the fetus. Partial monosomy 13q is a rare chromosomal disorder that results when a piece of the long arm (q) of chromosome 13 is missing (monosomic). Infants born with partial monosomy 13q may exhibit low birth weight, malformations of the head and face (craniofacial region), skeletal abnormalities (especially of the hands and feet), and other physical abnormalities. Mental retardation is characteristic of this condition. The mortality rate during infancy is high among individuals born with this disorder. Almost all cases of partial monosomy 13q occur randomly for no apparent reason (sporadic). 22q 11.2 deletion syndrome, also known as DiGeorge syndrome, is a syndrome caused by the deletion of a small piece of chromosome 22. The deletion (22 q 11.2) occurs near the middle of the chromosome on the long arm of one of the pair of chromosome. The features of this syndrome vary widely, even among members of the same family, and affect many parts of the body. Characteristic signs and symptoms may include birth defects such as congenital heart disease, defects in the palate, most commonly related to neuromuscular problems with closure (vela-pharyngeal insufficiency), learning disabilities, mild differences in facial features, and recurrent infections. Microdeletions in chromosomal region 22q 11.2 are associated with a 20 to 30-fold increased risk of schizophrenia. In one embodiment, a partial monosomy can be monosomy 18p, partial monosomy of chromosome 15 (15q11-q13), partial monosomy 13q, and partial monosomy of chromosome 22.

In one embodiment, the single individual having the aneuploidy is a fetus. In one embodiment, the single individual having the aneuploidy is the mother. Examples of aneuploidies that can be present in the mother include, but are not limited to, mosaic for a small supernumerary marker chromosome (SMC); t(1 1;14)(p15;p13) translocation; unbalanced translocation t(8; 11)(p23.2;p15.5); 1 1q23 microdeletion; SmithMagenis syndrome 17p1 1.2 deletion; 22q13.3 deletion; Xp22.3 microdeletion; 10p14 deletion; 20p microdeletion, DiGeorge syndrome [del(22)(q11.2q11.23)], Williams syndrome (7q11.23 and 7q36 deletions); 1p36 deletion; 2p microdeletion; neurofibromatosis type 1 (17q1 1.2 microdeletion), Y q deletion; Wolf-Hirschhorn syndrome (WHS, 4p16.3 microdeletion); 1p36.2 microdeletion; 11q14 deletion; 19q13.2 microdeletion; Rubinstein-Taybi (16 p13.3 microdeletion); 7p21 microdeletion; Miller-Dieker syndrome (17p13.3), 17p1 1.2 deletion; and 2q37 microdeletion.

In addition to the early determination of birth defects, the methods described herein can be applied to the determination of any abnormality in the representation of genetic sequences within the genome. It has been shown that blood plasma and serum DNA from cancer patients contains measurable quantities of tumor DNA, which can be recovered and used as a surrogate source of tumor DNA. Tumors are characterized by aneuploidy, or inappropriate numbers of gene sequences or even entire chromosomes. The determination of a difference in the amount of a given sequence i.e., a sequence of interest, in a sample from an individual can thus be used in the diagnosis of a medical condition e.g., a neoplasm. Examples of neoplasms include, but are not limited to, carcinoma, sarcoma, lymphoma, leukemia, germ cell tumors and blastoma. Specific cancers include, but are not limited to, lung cancer, breast cancer, and prostate cancer. Identification of genomic instabilities associated with cancers that can be determined in the circulating cfDNA in cancer patients is a potential diagnostic and prognostic tool. A sequence of interest includes one that is known or is suspected to play a role in the development and/or progression of the neoplasm. Examples of a sequence of interest include nucleic acids sequences that are amplified or deleted in cancerous cells as described herein.

It is believed that many solid tumors, such as breast cancer, progress from initiation to metastasis through the accumulation of several genetic aberrations. [Sato et al., Cancer Res., 50:7184-7189 [1990]; Jongsma et al., J Clin Pathol: Mol Path 55:305-309 [2002])]. Such genetic aberrations, as they accumulate, may confer proliferative advantages, genetic instability and the attendant ability to evolve drug resistance rapidly, and enhanced angiogenesis, proteolysis and metastasis. The genetic aberrations may affect either recessive "tumor suppressor genes" or dominantly acting oncogenes. Deletions and recombination leading to loss of heterozygosity (LOH) are believed to play a major role in tumor progression by uncovering mutated tumor suppressor alleles.

cfDNA has been found in the circulation of patients diagnosed with malignancies including but not limited to lung cancer (Pathak et al. Clin Chem 52: 1833-1842 [2006]), prostate cancer (Schwartzenbach et al. Clin Cancer Res 15:1032-8 [2009]), and breast cancer (Schwartzenbach et al. available online at breast-cancer-research.com/content/11/5/R71 [2009]). Identification of genomic instabilities associated with cancers that can be determined in the circulating cfDNA in cancer patients is a potential diagnostic and prognostic tool. In one embodiment, the method of the disclosure assesses CNV of a sequence of interest in a sample that includes a mixture of templates derived from a subject that is suspected or is known to have cancer e.g. carcinoma, sarcoma, lymphoma, leukemia, germ cell tumors and blastoma. In one embodiment, the sample is a plasma sample derived (processed) from peripheral blood and that includes a mixture of cfDNA derived from normal and cancerous cells. In another embodiment, the biological sample that is needed to determine whether a CNV is present is derived from a mixture of templates originating from cancerous and non-cancerous cells from other biological fluids including but not limited to serum, sweat, tears, urine, sputum, ear flow, lymph, saliva, cerebrospinal fluid, ravages, bone marrow suspension, vaginal flow, transcervical lavage, brain fluid, ascites, milk, secretions of the respiratory, intestinal and genitourinary tracts, and leukophoresis samples, or in tissue biopsies, swabs or smears.

Dominantly acting genes associated with human solid tumors typically exert their effect by overexpression or altered expression. Gene amplification is a common mechanism leading to upregulation of gene expression. Evidence from cytogenetic studies indicates that significant amplification occurs in over 50% of human breast cancers. Most notably, the amplification of the proto-oncogene human epidermal growth factor receptor 2 (HER2) located on chromosome 17 (17(17q21-q22)), results in overexpression of HER2 receptors on the cell surface leading to excessive and dysregulated signaling in breast cancer and other malignancies (Park et al., Clinical Breast Cancer 8:392-401 [2008]). A variety of oncogenes have been found to be amplified in other human malignancies. Examples of the amplification of cellular oncogenes in human tumors include amplifications of: c-myc in promyelocytic leukemia cell line HL60, and in small-cell lung carcinoma cell lines, N-myc in primary neuroblastomas (stages III and IV), neuroblastoma cell lines, retinoblastoma cell line and primary tumors, and small-cell lung carcinoma lines and tumors, L-myc in small-cell lung carcinoma cell lines and tumors, c-myb in acute myeloid leukemia and in colon carcinoma cell lines, c-erbb in epidermoid carcinoma cell, and primary gliomas, c-K-ras-2 in primary carcinomas of lung, colon, bladder, and rectum, N-ras in mammary carcinoma cell line (Varmus H., Ann Rev Genetics 18: 553-612 (1984) [cited in Watson et. al., Molecular Biology of the Gene (4th ed.; Benjamin/Cummings Publishing Co. 1987)].

Chromosomal deletions involving tumor suppressor genes may play an important role in the development and progression of solid tumors. The retinoblastoma tumor suppressor gene (Rb-1), located in chromosome 13q14, is the most extensively characterized tumor suppressor gene. The Rb-1 gene product, a 105 kDa nuclearphosphoprotein, apparently plays an important role in cell cycle regulation (Howe et al., Proc Natl Acad Sci (USA) 87:5883-5887 [1990]). Altered or lost expression of the Rb protein is caused by inactivation of both gene alleles either through a point mutation or a chromosomal deletion. Rb-i gene alterations have been found to be present not only in retinoblastomas but also in other malignancies such as osteosarcomas, small cell lung cancer (Rygaard et al., Cancer Res 50: 5312-5317 [1990])) and breast cancer. Restriction fragment length polymorphism (RFLP) studies have indicated that such tumor types have frequently lost heterozygosity at 13q suggesting that one of the Rb-1 gene alleles has been lost due to a gross chromosomal deletion (Bowcock et al., Am J Hum Genet, 46: 12 [1990]). Chromosome 1 abnormalities including duplications, deletions and unbalanced translocations involving chromosome 6 and other partner chromosomes indicate that regions of chromosome 1, in particular 1q21-1q32 and 1p1 1-13, might harbor oncogenes or tumor suppressor genes that are pathogenetically relevant to both chronic and advanced phases of myeloproliferative neoplasms (Caramazza et al., Eur J Hematol 84: 191-200 [2010]). Myeloproliferative neoplasms are also associated with deletions of chromosome 5. Complete loss or interstitial deletions of chromosome 5 are the most common karyotypic abnormality in myelodysplastic syndromes (MDSs). Isolated del(5q)/5q-MDS patients have a more favorable prognosis than those with additional karyotypic defects, who tend to develop myeloproliferative neoplasms (MPNs) and acute myeloid leukemia. The frequency of unbalanced chromosome 5 deletions has led to the idea that 5q harbors one or more tumor-suppressor genes that have fundamental roles in the growth control of hematopoietic stem/progenitor cells (HSCs/HPCs). Cytogenetic mapping of commonly deleted regions (CDRs) centered on 5q31 and 5q32 identified candidate tumor-suppressor genes, including the ribosomal subunit RPS14, the transcription factor Egrl/Krox20 and the cytoskeletal remodeling protein, alpha-catenin (Eisenmann et al., Oncogene 28:3429-3441 [2009]). Cytogenetic and allelotyping studies of fresh tumors and tumor cell lines have shown that allelic loss from several distinct regions on chromosome 3p, including 3p25, 3p21-22, 3p21.3, 3p12-13 and 3p14, are the earliest and most frequent genomic abnormalities involved in a wide spectrum of major epithelial cancers of lung, breast, kidney, head and neck, ovary, cervix, colon, pancreas, esophagous, bladder and other organs. Several tumor suppressor genes have been mapped to the chromosome 3p region, and are thought that interstitial deletions or promoter hypermethylation precede the loss of the 3p or the entire chromosome 3 in the development of carcinomas (Angeloni D., Briefings Functional Genomics 6:19-39 [2007]).

Newborns and children with Down syndrome (DS) often present with congenital transient leukemia and have an increased risk of acute myeloid leukemia and acute lymphoblastic leukemia. Chromosome 21, harboring about 300 genes, may be involved in numerous structural aberrations, e.g., translocations, deletions, and amplifications, in leukemias, lymphomas, and solid tumors. Moreover, genes located on chromosome 21 have been identified that play an important role in tumorigenesis. Somatic numerical as well as structural chromosome 21 aberrations are associated with leukemias, and specific genes including RUNX1, TMPRSS2, and TFF, which are located in 21q, play a role in tumorigenesis (Fonatsch C Gene Chromosomes Cancer 49:497-508 [2010]).

Other examples of a sequence of interest includes a pathogen sequence. A pathogen can be a prokaryotic pathogen, a eukaryotic pathogen, or a viral pathogen. Examples of prokaryotic pathogens include gram-negative pathogens and gram-positive pathogens. Examples of eukaryotic pathogens include fungal, yeast, and protozoan pathogens. The genomes of many pathogens are known and the selection of a specific sequence as a sequence of interest for use in identifying the presence of a pathogen is routine to the person of ordinary skill in the art. Examples of a sequence of interest also include a genetic variant, such as a single nucleotide polymorphism (SNP), an insertion, deletion, rearrangement, or a specific mutation of an allele. The identification of the presence or absence of such a sequence of interest can be used in a companion diagnostic test, for example, to predict whether a therapy will benefit a specific individual, to predict an effective dosage of a therapeutic, to monitor and/or adjust a therapy, and to tailor a therapy to a specific individual.

The sample can include high molecular weight material such as genomic DNA (gDNA). The sample can include low molecular weight material such as cfDNA. In another embodiment, low molecular weight material includes enzymatically or mechanically fragmented DNA.

In some embodiments, genomic DNA is used as the template, and it is fragmented into usable lengths, such as lengths of several hundred base pairs. In other embodiments, cfDNA is used as the template, and fragmentation is typically not required as cfDNA exists as short fragments. For example, fetal cfDNA circulates in the bloodstream as fragments of <300 bp, and maternal cfDNA has been estimated to circulate as fragments of between about 500 and 1,000 bp (Li et al., 2004, Clin Chem, 50: 1002-1011). Random fragmentation refers to the fragmentation of a polynucleotide molecule from a sample in a non-ordered fashion by enzymatic, chemical or mechanical means. Such fragmentation methods are known in the art and use standard methods (Sambrook and Russell, Molecular Cloning, A Laboratory Manual, third edition). In one embodiment, the fragmentation uses methods disclosed in Gunderson et al. (WO2016/130704). For the sake of clarity, generating smaller fragments of a larger piece of nucleic acid via specific PCR amplification of such smaller fragments is not equivalent to fragmenting the larger piece of nucleic acid because the larger piece of nucleic acid sequence remains in intact (i.e., is not fragmented by the PCR amplification). Moreover, random fragmentation is designed to produce fragments irrespective of the sequence identity or position of nucleotides including and/or surrounding the break. More particularly, the random fragmentation is by mechanical means such as nebulization or sonication to produce fragments of about 50 base pairs in length to about 1500 base pairs in length, still more particularly 50-700 base pairs in length, yet more particularly 50-400 base pairs in length. Most particularly, the method is used to generate smaller fragments of from 50-150 base pairs in length Fragmentation of polynucleotide molecules by mechanical means (nebulization, sonication, and/or Hydroshear, for example) results in fragments with a heterogeneous mix of blunt and 3'- and 5'-overhanging ends, including ends lacking 5' phosphates. Moreover, cfDNA also includes a heterogeneous mix of blunt and 3'- and 5'-overhanging ends. In some embodiments it is therefore desirable to repair the ends of templates to be used in methods described herein by end-repairing. End-repairing can be accomplished using methods or kits known in the art to generate ends that are optimal for insertion, for example, into blunt sites of cloning vectors. In one embodiment, the fragment ends of the population of nucleic acids are blunt ended, and optionally the fragment ends are also phosphorylated. The phosphate moiety can be introduced via enzymatic treatment, for example, using polynucleotide kinase.

In one embodiment, the templates are prepared with single overhanging nucleotides by tailing. Tailing can be accomplished, for example, using certain types of DNA polymerase such as Taq polymerase or Klenow exo minus polymerase which has a nontemplate-dependent terminal transferase activity that adds a single deoxynucleotide, for example, deoxyadenosine (A) to the 3' ends of a DNA molecule, for example, a PCR product. Such enzymes can be used to add a single nucleotide 'A' to the blunt ended 3' terminus of each strand of the double-stranded target fragments. Thus, an 'A' could be added to the 3' terminus of each end repaired strand of the double-stranded target fragments by reaction with Taq or Klenow exo minus polymerase, while universal adaptor could be a T-construct with a compatible 'T' overhang present on the 3' terminus of each region of double-stranded nucleic acid of the universal adaptor. This end modification also prevents self-ligation such that there is a bias towards formation of the combined ligated adaptor-template-adaptor molecules.

A template described herein can include a universal adaptor at each end, and such a molecule is referred to herein as an adaptor-template-adaptor molecule. Methods for making an adaptor-template-adaptor molecule include attaching a universal adaptor to each end of double-stranded template molecules. The double-stranded template molecules can be from a control sample (FIG. 1, block 10), a test sample (FIG. 1, block 14), or a population of reDNA fragments, for instance a library (FIG. 1, block 13). The attachment can be through standard library preparation techniques using ligation.

In one embodiment, the double-stranded template nucleic acids are treated by first ligating identical universal adaptor molecules to form adaptor-template-adaptor molecules. The universal adaptor molecules include a region of double-stranded nucleic acid. In one embodiment, the universal adaptor also includes a region of single-stranded non-complementary nucleic acid strands. A universal adaptor having a double-stranded and a single stranded region is also referred to as a "mismatched adaptor," the general features of which are defined below, and further described in Gormley et al., (U.S. Pat. No. 7,741,463) and Bignell et al., (U.S. Pat. No. 8,053,192).

The double-stranded region of the universal adapter is a short double-stranded region, typically including 5 or more consecutive base pairs. This term refers to a double-stranded region of nucleic acid in which the two strands are annealed and does not imply any particular structural conformation. As used herein, the term "double-stranded," when used in reference to a nucleic acid molecule, means that substantially all of the nucleotides in the nucleic acid molecule are hydrogen bonded to a complementary nucleotide. It will be appreciated that one or more nucleotide mismatches may be tolerated within the double-stranded region, provided that the two strands can form a stable duplex under standard ligation conditions. A partially double-stranded nucleic acid can have at least 10%, at least 25%, at least 50%, at least 60%, at least 70%, at least 80%, at least 90%, or at least 95% of its nucleotides hydrogen bonded to a complementary nucleotide. In one embodiment, the two strands of the universal adapter are 100% complementary in the double-stranded region.

Generally, it is advantageous for the double-stranded region to be as short as possible without loss of function. In this context, "function" refers to the ability of the double-stranded region to form a stable duplex under standard reaction conditions for an enzyme-catalyzed nucleic acid ligation reaction, which is known to the skilled reader (e.g., incubation at a temperature in the range of 4° C. to 25° C. in a ligation buffer appropriate for the enzyme), such that the two strands forming the universal adapter remain partially annealed during ligation of the universal adapter to a template molecule. It is not necessary for the double-stranded region to be stable under the conditions typically used in the annealing steps of primer extension or PCR reactions.

Because identical universal adapters are ligated to both ends of each target molecule, the template sequence in each adaptor-template-adaptor molecule will be flanked by complementary sequences derived from the double-stranded region of the universal adapters. The longer the double-stranded region, and hence the complementary sequences derived therefrom in the adaptor-template-adaptor constructs, the greater the possibility that the adaptor-template-adaptor construct is able to fold back and base-pair to itself in these regions of internal self-complementarity under the annealing conditions used in primer extension and/or PCR. It is, therefore, generally preferred for the double-stranded region to be no greater than 20, no greater than 15, or no greater than 10 base pairs in length in order to reduce this effect. In some embodiment, the stability of the double-stranded region may be increased, and hence its length potentially reduced, by the inclusion of non-natural nucleotides which exhibit stronger base-pairing than standard Watson-Crick base pairs.

Universal adaptors for use herein will generally include a double-stranded region forming the "ligatable" end of the adaptor, i.e., the end that is joined to a double-stranded target fragment in the ligation reaction. The ligatable end of the universal adaptor may be blunt or, in other embodiments, short 5' or 3' overhangs of one or more nucleotides may be present to facilitate/promote ligation. The 5' terminal nucleotide at the ligatable end of the universal adapter is typically phosphorylated to enable phosphodiester linkage to a 3' hydroxyl group on the target polynucleotide.

The double-stranded region of a universal adaptor typically includes a universal removal sequence and a universal primer binding site. In some embodiments, a universal removal sequence can be used as a universal primer binding site. Optionally one or more other universal sequences such as a universal extension primer binding site can be present.

A universal removal sequence, also referred to as a removal sequence, is a nucleotide sequence that can be used to remove a universal adaptor from the template to which it is bound, e.g., use of a removal sequence can help convert an adaptor-template-adaptor molecule to three separate molecules: a template and two universal adaptors. Other methods for removing universal adaptors include the use of non-natural nucleotides, and non-natural backbone linkages. A universal adaptor may include mixtures of natural and non-natural nucleotides, optionally linked by a mixture of phosphodiester and non-phosphodiester backbone linkages. Other non-nucleotide modifications may be included to facilitate cleavage of universal adaptors from an adaptor-template-adaptor molecule. Such non-natural nucleotides and linkages can be introduced into a universal adaptor during amplification of adaptor-template-adaptor molecules, as described in detail herein.

In one embodiment, a removal sequence includes a restriction endonuclease recognition sequence. A restriction endonuclease recognition sequence is a nucleotide sequence to which a restriction endonuclease can bind. Any restriction endonuclease can be used, and the recognition sequence for any useful restriction endonuclease is known to the skilled person. In one embodiment, a restriction endonuclease is a Type II, a Type III, or a Type IV enzyme. In one embodiment, a restriction endonuclease is one that cleaves a double-stranded DNA at the recognition site. In another embodiment, a restriction endonuclease is one that cleaves a double-stranded DNA at a specific distance from the recognition site. For example, in some embodiments, a restriction endonuclease is one that cleaves off the recognition site from the remaining fragment. Examples of useful restriction endonucleases that cleave a double-stranded DNA near the recognition site include, but are not limited to, MlyI, SapI, and BpuEI.

The skilled person will recognize that using a restriction endonuclease that cleaves at a specific distance from the recognition site permits control over the composition of the final products, i.e., the template and the universal adaptor, after removal. In one embodiment where the removal sequence is a recognition site for an endonuclease that cleaves at a specific distance from the recognition site, the recognition site can be placed in the double-stranded region to result in removal of all universal adaptor sequences (e.g., the template molecule that results after removal of the universal adaptors is identical to the template that was used to produce the adaptor-template-adaptor molecule). In another embodiment where the removal sequence is a recognition site for an endonuclease that cleaves at a specific distance from the recognition site, the recognition site can be placed in the double-stranded region to result in removal of some universal adaptor sequences (e.g., the template molecule that results after removal of the universal adaptors is the template and a portion of the universal adaptor that was used to produce the adaptor-template-adaptor molecule). In yet another embodiment where the removal sequence is a recognition site for an endonuclease that cleaves at a specific distance from the recognition site, the recognition site can be placed in the double-stranded region to result in removal of all universal adaptor sequences and some of the template sequences located at each end and adjacent to a universal adaptor (e.g., the template molecule that results after removal of the universal adaptors is a non-naturally occurring and shorter version of the template that was used to produce the adaptor-template-adaptor molecule).

In one embodiment, the universal adaptor also includes a region of single-stranded non-complementary nucleic acid strands. This region, also referred to as an "unmatched region," refers to a region where the sequences of the two polynucleotide strands forming the universal adaptor exhibit a degree of non-complementarity such that the two strands are not capable of fully annealing to each other under standard annealing conditions for a primer extension or PCR reaction. The unmatched region may exhibit some degree of annealing under standard reaction conditions for an enzyme-catalyzed ligation reaction, provided that the two strands revert to single stranded form under annealing conditions in an amplification reaction. In one embodiment, the addition of adaptors to reDNA and to fragmented nucleic acids from a test sample (FIG. 1, block 15) results in addition of universal adaptors having both a double-stranded region and a single-stranded region. The addition may be in one step (e.g., ligation of a universal adaptor having both a double-stranded region and a single-stranded region) or more than one step (e.g., ligation of a universal adaptor having a double-stranded region followed by amplification to add a single-stranded region).

Mismatches in the unmatched region can take the form of one strand being longer than the other, such that there is a single stranded region on one of the strands, or a sequence selected such that the two strands do not hybridize, and thus form a single stranded region on both strands. The mismatches may also take the form of "bubbles," where both ends of the universal adapter construct are capable of hybridizing to each other and forming a duplex, but the central region is not. The portion of the strand(s) forming the unmatched region are not annealed under conditions in which other portions of the same two strands are annealed to form one or more double-stranded regions. For avoidance of doubt it is to be understood that a single-stranded or single base overhang at the 3' end of a polynucleotide duplex that subsequently undergoes ligation does not constitute an "unmatched region" in the context of this disclosure.

The region of single-stranded non-complementary nucleic acid strands typically includes at least one universal extension primer binding site. A universal primer extension binding site can be used to capture multiple different nucleic acids, e.g., multiple different adapter-template-adapter molecules using a population of universal capture nucleic acids that are complementary to the universal primer extension binding site.

Optionally, one or more other universal sequences can be present. In one embodiment, the region of single-stranded non-complementary nucleic acid strands also includes at least one sample-specific index. A sample-specific index can be used as a marker characteristic of the source of particular templates on an array. Generally, the sample-specific index is a synthetic sequence of nucleotides that is part of the universal adapter which is added to the templates as part of a library preparation step. Accordingly, a sample-specific index is a nucleic acid sequence which is attached to each of the template molecules of a particular sample, the presence of which is indicative of, or is used to identify, the sample from which the template molecules were isolated.

Preferably the sample-specific index may be up to 20 nucleotides in length, more preferably 1-10 nucleotides, and most preferably 4-6 nucleotides in length. A four nucleotide index gives a possibility of multiplexing 256 samples on the same array, a six base tag enables 4096 samples to be processed on the same array.

The lower limit on the length of the unmatched region will typically be determined by function, for example, the need to provide a suitable sequence for i) binding of a primer for primer extension, PCR and/or sequencing (for instance, binding of a primer to a universal primer binding site), or for ii) binding of a universal capture nucleic acid for immobilization of an adapter-template-adapter to a surface (for instance, binding of a universal capture nucleic acid to a universal primer extension binding site). Theoretically there is no upper limit on the length of the unmatched region, except that in general it is advantageous to minimize the overall length of the universal adapter, for example, to facilitate separation of unbound universal adapters from adaptor-template-adaptor constructs following the ligation step. Therefore, it is generally preferred that the unmatched region should be less than 50, or less than 40, or less than 30, or less than 25 consecutive nucleotides in length.

Although the precise nucleotide sequence of the universal adapter is generally non-limiting to the disclosure, the sequences of the individual strands in the unmatched region should be such that neither individual strand exhibits any internal self-complementarity which could lead to self-annealing, formation of hairpin structures, etc. under standard annealing conditions. Self-annealing of a strand in the unmatched region is to be avoided as it may prevent or reduce specific binding of a primer to this strand.

In one embodiment, the universal adaptor includes all sequences necessary for the subsequent removal of the adaptors from adaptor-template-adaptor molecules (FIG. 1, block 13). In one embodiment, the universal adaptor includes all sequences necessary for immobilizing the adapter-template-adapter molecules on an array for subsequent amplification and/or sequencing (FIG. 1, block 16). In another embodiment, an amplification step is used to further modify the universal adapter present in each adaptor-template-adaptor molecule prior to immobilizing and sequencing (FIG. 1, block 16). For instance, in those embodiments where the nucleotide sequence of a portion of the template is to be determined, an initial primer extension reaction can be carried out using a universal primer binding site in which extension products complementary to both strands of each individual adapter-template-adapter molecule are formed and add a universal extension primer site. The resulting primer extension products, and optionally amplified copies thereof, collectively provide a library of template polynucleotides that can be immobilized and then sequenced.

Ligation methods can be used to join a universal adaptor to a template. Ligation methods useful herein are known in the art and use standard methods. Such methods use ligase enzymes such as DNA ligase to effect or catalyze joining of the ends of the two polynucleotide strands of, in this case, the universal adapter and the double-stranded templates, such that covalent linkages are formed. The universal adapter may contain a 5'-phosphate moiety to facilitate ligation to the 3'-OH present on a template. The double-stranded template contains a 5'-phosphate moiety, either residual or added using an enzymatic treatment step, and has been end repaired, and optionally extended by an overhanging base or bases, to give a 3'-OH suitable for ligation. In this context, joining means covalent linkage of polynucleotide strands which were not previously covalently linked. In a particular aspect of the disclosure, such joining takes place by formation of a phosphodiester linkage between the two polynucleotide strands, but other means of covalent linkage (e.g. non-phosphodiester backbone linkages) may be used.

Figure 3:
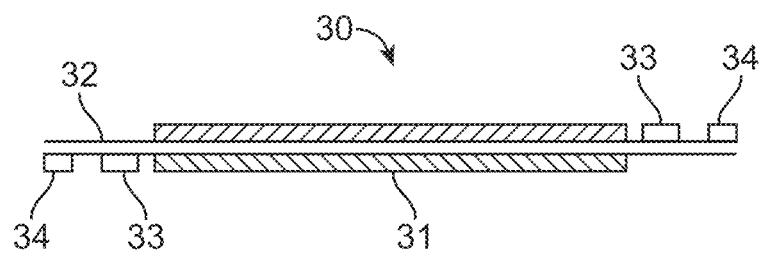
FIG. 3 shows a schematic drawing of an adaptor-template-adaptor molecule 30 that can be produced in accordance with various embodiments described herein. The depicted molecule 30 includes a double-stranded template region 31 and a universal adaptor 32 attached at each end. In the depicted embodiment, the universal adaptor 32 includes a universal removal sequence 33 and a universal primer binding site 34.
Figure 4:
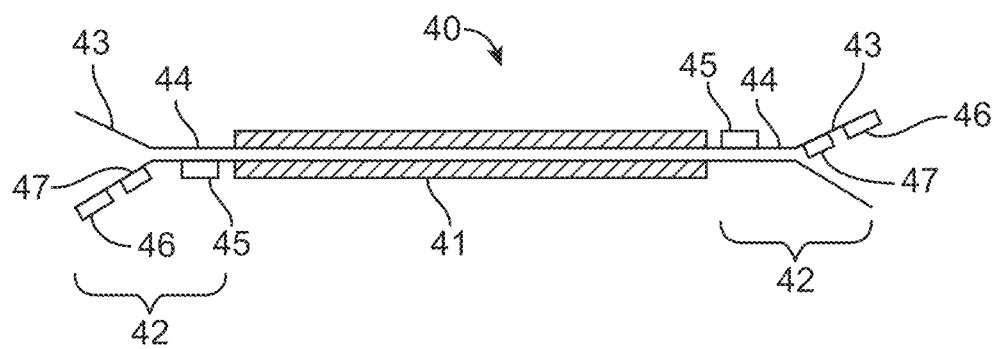
FIG. 4 shows a schematic drawing of an adaptor-template-adaptor molecule 40 that can be produced in accordance with various embodiments described herein. The depicted molecule 40 includes a double-stranded template region 41 and a universal adaptor 42 attached at each end. The universal adaptor includes a single-stranded region 43 and a double-stranded region 44, In the depicted embodiment, the universal adaptor 42 includes a universal removal sequence 45, a universal extension primer binding site 46, and a sample-specific index 47.

As discussed herein, in one embodiment, universal adaptors used in the ligation are complete. For instance, when universal adaptors are being added to produce a reDNA library (FIG. 1, block 11), the universal adaptor can include a double-stranded region and universal sequences such as a universal primer binding site, a universal removal sequence, or a combination thereof (FIG. 3). When universal adaptors are being added to a population of reDNA fragments or fragmented nucleic acids from a test sample (FIG. 1, bock 15), the universal adaptor can include double-stranded and single-stranded regions that contain, for instance, a universal removal sequence, a universal primer binding site, a universal extension primer binding site, a sample-specific index, or a combination thereof (FIG. 4). The skilled person will readily appreciate the advantage of using different universal adaptors for addition to reDNA and test sample DNA, as the use of different indexes for each population of fragments will allow identification of the source of the template molecules later after sequencing. The plurality of adaptor-template-adaptor molecules can be used to prepare immobilized samples for sequencing (FIG. 1, block 16).

Figure 5:
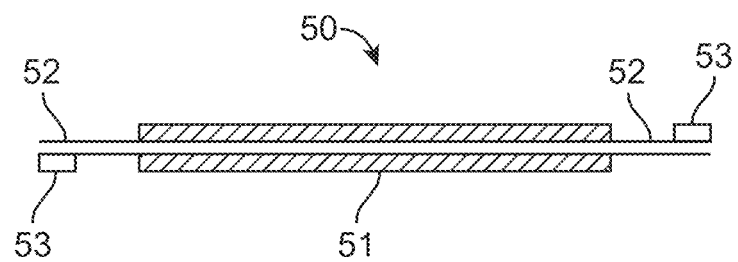
FIG. 5 shows a schematic drawing of an adaptor-template-adaptor molecule 50 that can be produced in accordance with various embodiments described herein. The depicted molecule 50 includes a double-stranded template region 51 and a universal adaptor 52 attached at each end. In the depicted embodiment, the universal adaptor 52 includes a universal primer binding site 53.
Figure 6:
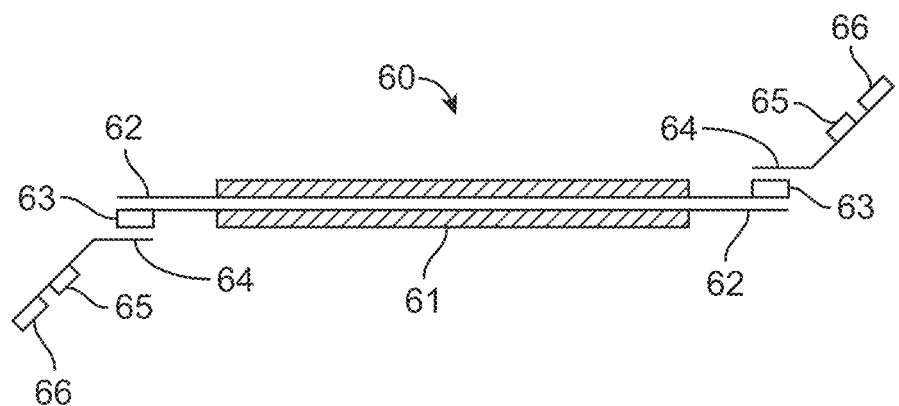
FIG. 6 shows a schematic drawing of an adaptor-template-adaptor molecule 60 that can be produced in accordance with various embodiments described herein. The depicted molecule 60 includes a double-stranded template region 61 and a universal adaptor 62 attached at each end. In the depicted embodiment, the universal adaptor 62 includes a universal primer binding site 63. A universal primer 64 that binds to the universal primer binding site 63 is also shown in the depicted embodiment. In the depicted embodiment, the universal primer 64 includes a sample-specific index 65 and a universal extension primer binding site 66.

Also as discussed herein, in one embodiment, universal adaptors used in the ligation include a double-stranded region which may have universal sequences, such as a universal primer binding site (FIG. 5). The resulting plurality of adapter-template-adapter molecules (FIG. 1, block 15) can be further modified to include additional universal sequences, such as a universal extension primer binding site and a sample-specific index (FIG. 6). Methods for addition of specific sequences, such as a universal extension primer binding site, to universal primers that are ligated to double-stranded target fragments include PCR based methods, and are known in the art and are described in, for instance, Bignell et al. (U.S. Pat. No. 8,053,192) and Gunderson et al. (WO2016/130704).

In those embodiments where a universal adapter is modified to include additional universal sequences, an amplification reaction is prepared. The contents of an amplification reaction are known to one skilled in the art and include appropriate substrates (such as dNTPs), enzymes (e.g. a DNA polymerase) and buffer components required for an amplification reaction. Generally amplification reactions require at least two amplification primers, often denoted "forward" and "reverse" primers (primer oligonucleotides) that are capable of annealing specifically to a part of the polynucleotide sequence to be amplified under conditions encountered in the primer annealing step of each cycle of an amplification reaction. In certain embodiments the forward and reverse primers may be identical. Thus, the universal primer includes a 'universal primer binding site-specific portion,' being a sequence of nucleotides capable of annealing to a universal sequence such as a universal primer binding site, in the polynucleotide molecule to be amplified (or the complement thereof if the template is viewed as a single strand) during the annealing step.

Depending on the embodiment of the disclosure, the universal primers may be universal for all samples, or one of the forward or reverse primers may carry the index sequence that codes for the sample source. The universal primers may hybridize across the index region of the ligated adaptor, in which case it is advantageous to use unique primers for each sample nucleic acid. The amplification reaction may be performed with more than two universal primers. In order to prevent the amplification of ligated adapter-adapter dimers, the universal primers can be modified to contain nucleotides that hybridize across the whole of the ligated adapter and into the ligated template (or the dNTP's attached to the 3' end thereof). This first universal primer can be modified and treated to help prevent exonuclease digestion of the strands, and thus it may be advantageous to have a first universal primer that can amplify all samples rather than modifying and treating each of the indexed primers separately. The indexed primer can be introduced as a sample specific third primer in the amplification reaction, but does not need to be specially modified and treated to reduce exonuclease digestion. In the case of this embodiment the third universal primer that carries the index can contain a sequence that is the same as at least a portion of the first universal primer such that it can be used to amplify the duplex resulting from extension of the first universal primer.

In the context of the present disclosure, the term 'polynucleotide molecule to be amplified' refers to the original or starting adaptor-template-adaptor sequence added to the amplification reaction. The 'universal primer binding site-specific portion' in the forward and reverse universal primers refers to a sequence capable of annealing to the original or initial adaptor-template-adaptor present at the start of the amplification reaction and reference to the length of the 'universal primer binding site-specific portion' relates to the length of the sequence in the primer which anneals to the starting adaptor-template-adaptor molecule. It will be appreciated that if the primers contain any nucleotide sequence which does not anneal to the starting adaptor-template-adaptor molecule in the first amplification cycle then this sequence may be copied into the amplification products. Hence the amplified adaptor-template-adaptor molecules produced in the first and subsequent cycles of amplification may be longer than the starting adaptor-template-adaptor molecules.

Because the mismatched adapters can be different lengths, the length of adapter sequence added to the 3' and 5' ends of each strand may be different. The universal primers may also be of different lengths to each other, and may hybridize to different lengths of the adapter, and therefore the length added to the ends of each strand can be controlled. In the case of nested PCR, the three or more universal primers can be designed to be longer than the primer used to amplify the previous amplicon, so the length of the added nucleotides is fully controllable and may be hundreds of base pairs if desired. In one embodiment, the first universal primer adds 13 bases to the ligated adapter, and the third universal primer adds a further 27 bases such that one end of the amplicon is 40 bases longer than the short arm of adapter-target construct. The short arm of the adapter is 20 bases in length, meaning that the prepared template includes the template plus 60 added bases at the end. The second universal primer is 25 bases longer than the long arm of adapter, which is 32 bases in length plus the additional T that hybridizes across the dATP nucleoside added to the sample. Thus, the prepared template comprises the genomic fragment, plus the added dATP, plus 57 known bases. Thus in full, one strand of each template duplex comprises from the 5' end: 60 known bases, T, the genomic fragment, A, 57 known bases-3' end. This strand is fully complementary to a sequence: 5'-57 known bases, T, genomic fragment, A, 60 known bases-3' end. The length 57 and 60 are arbitrary, and shown for the purpose of clarification, and should not be viewed as limiting. The length of the added sequences may be 20-100 bases or more depending on the desired experimental design.

The forward and reverse primers may be of sufficient length to hybridize to the whole of the adaptor sequence and at least one base of the target sequence (or the nucleotide dNTP added as a 3'-overhang on the target strands). The forward and reverse primers may also contain a region that extends beyond the adaptor construct, and therefore the universal primers may be at least 20-100 bases in length. The forward and reverse primers may be of significantly different lengths; for example, one may be 20-40 bases, whereas the other one may be 40-100 bases in length. The nucleotide sequences of the universal adaptor specific portions of the forward and reverse primers are selected to achieve specific hybridization to the adaptor-template-adaptor molecules to be amplified under the conditions of the annealing steps of the amplification reaction, while minimizing non-specific hybridization to any other target sequences present.

Skilled readers will appreciate that it is not strictly required for the universal adaptor specific portion to be 100% complementary, as a satisfactory level of specific annealing can be achieved with less than perfectly complementary sequences. In particular, one or two mismatches in the universal adaptor specific portion can usually be tolerated without adversely affecting specificity. Therefore, the term 'universal primer binding site-specific portion,' should not be interpreted as requiring 100% complementarity with the universal adaptor of an adaptor-template-adaptor molecule. However, the requirement that the primers do not anneal non-specifically to regions of the adaptor-template-adaptor other than their respective primer-binding sequences must be fulfilled.

Universal primers are generally single stranded polynucleotide structures. They may also contain a mixture of natural and non-natural bases and also natural and non-natural backbone linkages, provided that any non-natural modifications do not preclude function as a primer—that being the ability to anneal to a polynucleotide strand during conditions of the amplification reaction and to act as an initiation point for synthesis of a new complementary polynucleotide.

As discussed herein, methods of the present disclosure can include removal of universal adaptors from adaptor-template-adaptor molecules (FIG. 1, block 13). In one embodiment, the universal adaptors can be removed by using a universal removal sequence. In another embodiment, chemical cleavage methods, including, but not limited to, cleavage of abasic sites, cleavage of ribonucleotides, photochemical cleavage, cleavage of hemi-methylated DNA, cleavage of a linker (e.g., peptide linker, pH sensitive linker, heat sensitive linker), methylation, or physical force may be used to remove universal adaptors from adaptor-template-adaptor molecules. These other methods typically include the use of non-natural nucleotides, non-natural backbone linkages, or a combination thereof. Thus, in one embodiment, a universal primer can include a mixture of natural and non-natural nucleotides, a mixture of phosphodiester and non-phosphodiester backbone linkages, other non-nucleotide modifications, or a combination thereof, to facilitate cleavage of universal adaptors from an adaptor-template-adaptor molecule. Use of a universal primer containing such alternative nucleotides, linkages, and/or modifications results in adaptor-template-adaptor molecules containing the alternative nucleotides, linkages, and/or modifications.

The term "chemical cleavage" encompasses any method which uses a non-nucleic acid and/or non-enzymatic chemical reagent to promote/achieve cleavage of one or both strands of a double-stranded adaptor-template-adaptor molecule. If required, one or both strands of the adaptor-template-adaptor molecule may include one or more non-nucleotide chemical moieties and/or non-natural nucleotides and/or non-natural backbone linkages in order to permit a chemical cleavage reaction at a pre-determined cleavage site. Typically, a site suitable for chemical cleavage is introduced into an adaptor-template-adaptor molecule using universal primers that include the site.

In one embodiment, one strand of an adaptor-template-adaptor molecule may include a diol linkage (see e.g., US2012/0270739) which permits cleavage by treatment with periodate (e.g. sodium periodate). The diol linkage may be positioned at a pre-determined cleavage site, the precise location of which may be selected by the user. It will be appreciated that more than one diol could be included at the cleavage site.

Diol linker units based on phosphoramidite chemistry suitable for incorporation into polynucleotide chains are commercially available (e.g., from Fidelity systems Inc., Gaithersburg, Md., USA). One or more diol units may be incorporated into a polynucleotide for use as a primer using standard methods for automated chemical DNA synthesis.

The diol linker is cleaved by treatment with a "cleaving agent," which can be any substance which promotes cleavage of the diol. The preferred cleaving agent is periodate, preferably aqueous sodium periodate ($NaIO_4$). Following treatment with the cleaving agent (e.g. periodate) to cleave the diol, the cleaved product may be treated with a "capping agent" in order to neutralize reactive species generated in the cleavage reaction. Suitable capping agents for this purpose include amines, such as ethanolamine. Advantageously, the capping agent (e.g. ethanolamine) may be included in a mixture with the cleaving agent (e.g. periodate) so that reactive species are capped as soon as they are formed.

An "abasic site" is defined as a nucleoside position in a polynucleotide chain from which the base component has been removed. Abasic sites can occur naturally in DNA under physiological conditions by hydrolysis of nucleoside residues, but may also be formed chemically under artificial conditions or by the action of enzymes. Once formed, abasic sites may be cleaved (e.g. by treatment with an endonuclease or other single-stranded cleaving enzyme, exposure to heat or alkali), providing a means for site-specific cleavage of a polynucleotide strand.

In a preferred but non-limiting embodiment an abasic site may be created at a pre-determined position of the universal adaptors of an adaptor-template-adaptor molecule. A universal primer is used that includes a deoxyuridine (U) at a pre-determined cleavage site. The enzyme uracil DNA glycosylase (UDG) can then be used to remove the uracil base from the members of an amplified reDNA library, generating an abasic site on one strand. The polynucleotide strand including the abasic site may then be cleaved at the abasic site by treatment with endonuclease (e.g EndoIV endonuclease, AP lyase, FPG glycosylase/AP lyase, EndoVIII glycosylase/AP lyase), heat, or alkali.

Abasic sites may also be generated at non-natural/modified deoxyribonucleotides other than deoxyuridine and cleaved in an analogous manner by treatment with endonuclease, heat, or alkali. For example, a universal primer can include 8-oxo-guanine or deoxyinosine. 8-oxo-guanine can be converted to an abasic site by exposure to FPG glycosylase. Deoxyinosine can be converted to an abasic site by exposure to AlkA glycosylase. The abasic sites thus generated may then be cleaved, typically by treatment with a suitable endonuclease (e.g. EndoIV, AP lyase).

In one embodiment, the double-stranded nucleic acid molecules to be cleaved may be exposed to a mixture containing the appropriate glycosylase (to generate the abasic site) and one or more suitable endonucleases (to subsequently cleave). In such mixtures the glycosylase and the endonuclease will typically be present in an activity ratio of at least about 2:1. In a particular embodiment, the USER reagent available from New Englad Biolabs (NEB #M5505S) is used for the creation of a single nucleotide gap at a uracil base.

In one embodiment, a universal primer can be used that includes one or more ribonucleotides. Incorporation of one or more ribonucleotides into a polynucleotide strand that otherwise includes deoxyribonucleotides (with or without additional non-nucleotide chemical moieties, non-natural bases or non-natural backbone linkages) can provide a pre-determined site for cleavage using a chemical agent capable of selectively cleaving the phosphodiester bond between a deoxyribonucleotide and a ribonucleotide or using a ribonuclease (RNAse). In one embodiment, the strand to be cleaved contains a single ribonucleotide to provide a pre-determined site for chemical cleavage.

Suitable chemical cleavage agents capable of selectively cleaving the phosphodiester bond between a deoxyribonucleotide and a ribonucleotide include metal ions, for example rare-earth metal ions (especially $La^+$, particularly $Tm^+$, $Yb^+$ or $Lu^+$ (Chen et al. Biotechniques. 2002, 32: 518-520; Komiyama et al. Chem. Commun. 1999, 1443-1451)), Fe(3) or Cu(3), or exposure to elevated pH, e.g. treatment with a base such as sodium hydroxide. By "selective cleavage of the phosphodiester bond between a deoxyribonucleotide and a ribonucleotide" is meant that the chemical cleavage agent is not capable of cleaving the phosphodiester bond between two deoxyribonucleotides under the same conditions.

The base composition of the ribonucleotide(s) is generally not material, but can be selected in order to optimize chemical (or enzymatic) cleavage. By way of example, rUMP or rCMP are generally preferred if cleavage is to be carried out by exposure to metal ions, especially rare earth metal ions.

The phosphodiester bond between a ribonucleotide and a deoxyribonucleotide, or between two ribonucleotides can also be cleaved by an RNase. Any endocytic ribonuclease of appropriate substrate specificity can be used for this purpose. For cleavage with ribonuclease it is preferred to include two or more consecutive ribonucleotides, and preferably from 2 to 10 or from 5 to 10 consecutive ribonucleotides. The precise sequence of the ribonucleotides is generally not material, except that certain RNases have specificity for cleavage after certain residues. Suitable RNases include, for example, RNaseA, which cleaves after C and U residues. Hence, when cleaving with RNaseA the cleavage site must include at least one ribonucleotide which is C or U.

Universal primers incorporating one or more ribonucleotides can be readily synthesized using standard techniques for oligonucleotide chemical synthesis with appropriate ribonucleotide precursors.

The term "photochemical cleavage" encompasses any method which utilises light energy in order to achieve cleavage of one or both strands of the double-stranded nucleic acid molecule.

A pre-determined site for photochemical cleavage can be provided by a non-nucleotide chemical spacer unit in one of the strands of the double-stranded molecule. Suitable photochemical cleavable spacers include the PC spacer phosphoamidite (4-(4,4'-Dimethoxytrityloxy)butyramidomethyl)-1-(2-nitrophenyl)-ethyl]-2-cyanoethyl-(N,N-diisopropyl)-phosphoramidite) supplied by Glen Research, Sterling, Va., USA (cat number 10-4913-XX) which has the structure:

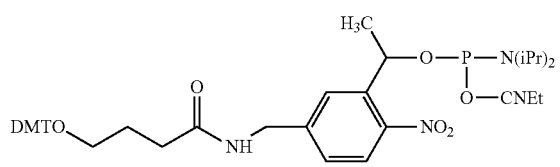

The spacer unit can be cleaved by exposure to a UV light source.

This spacer unit can be attached to the 5' end of a polynucleotide, together with a thiophosphate group which permits attachment to a solid surface, using standard techniques for chemical synthesis of oligonucleotides. Conveniently, this spacer unit can be incorporated into a forward or reverse amplification primer to be used for synthesis of a photocleavable double-stranded nucleic acid molecule by solid-phase amplification.

Site-specific cleavage of one strand of a double-stranded nucleic acid molecule may also be achieved by using a universal primer that incorporates one or more methylated nucleotides, and then cleaving the members of an amplified reDNA library with an endonuclease enzyme specific for a recognition sequence including the methylated nucleotide(s).

The methylated nucleotide(s) will typically be incorporated in a region of one strand of the double-stranded adaptor-template-adaptor molecule having a complementary stretch of non-methylated deoxyribonucleotides on the complementary strand, such that annealing of the two strands produces a hemimethylated duplex structure. The hemimethylated duplex may then be cleaved by the action of a suitable endonuclease.

Universal primers incorporating one or methylated nucleotides may be prepared using standard techniques for automated DNA synthesis, using appropriately methylated nucleotide precursors.

Primers may additionally comprise non-nucleotide chemical modifications, for example phosphorothioates having backbone modifications to increase exonuclease resistance, again provided such that modifications do not prevent primer function. Modifications may, for example, facilitate attachment of the primer to a solid support, for example a biotin moiety. Certain modifications may themselves improve the function of the molecule as a primer, or may provide some other useful functionality, such as providing a site for cleavage to enable the primer (or an extended polynucleotide strand derived therefrom) to be cleaved from a solid support (see, for instance, U.S. Pat. No. 9,085,802).

In an embodiment where an index is attached to a universal adaptor, the amplification can be carried out on either the pooled or unpooled samples. In an embodiment, an index is part of a universal primer, and therefore, each sample is amplified independently prior to pooling. The pooled nucleic acid samples can then be processed for sequencing.

After removal of adaptors from adaptor-template-adaptor molecules (FIG. 1, block 13) to yield reDNAs, the sample can be exposed to conditions to separate removed adaptors from template molecules. Separation of the desired reDNAs from removed adaptors can be aided by use of a capture agent. In one embodiment, a capture agent is added to adaptor-template-adaptor molecules during the amplification of adaptor-template-adaptor molecules (FIG. 1, block 12). For instance, the universal primers used to amplify adaptor-template-adaptor molecules can include a capture agent, such as a member of a receptor-ligand binding pair. Examples of useful receptor-ligand binding pairs include, but are not limited to, avidin, streptavidin, biotin, lectin, carbohydrate, nucleic acid binding protein, and, antibody.

In one embodiment, the amplified adaptor-template-adaptor molecules include a capture agent that is a ligand. The amplified adaptor-template-adaptor molecules are exposed to conditions that remove the adaptors (e.g., exposure to a restriction endonuclease when the universal removal sequence is a restriction endonuclease site). In one embodiment, the mixture of reDNAs and removed (unattached) adaptors is then exposed to the ligand's receptor under conditions suitable for binding of the ligand and receptor, and the removed adaptors that are bound to the receptor are separated from the reDNAs. In one embodiment, the receptor is bound to a surface or further includes a second ligand that can be used to separate the attached adaptors. In another embodiment, the amplified adaptor-template-adaptor molecules are contacted with a surface that includes the ligand's receptor, and the amplified adaptor-template-adaptor molecules become bound to the surface at one or both ends of the molecule. Subsequent exposure of the bound amplified adaptor-template-adaptor molecules to conditions that remove the adaptors (e.g., exposure to a restriction endonuclease when the universal removal sequence is a restriction endonuclease site) results in the removed adaptors bound to the surface and free templates, i.e., reDNAs. The surface can be an inert substrate or matrix (e.g., plastic, glass) of any suitable shape (flat, such as a slide, or curved, such as a bead).

In another embodiment, conditions useful to separate removed adaptors from template molecules include conditions that select for a predetermined size range, such as from 150 to 400 nucleotides in length, or from 150 to 300 nucleotides. Methods for selecting a predetermined size range include, but are not limited to, gel-electrophoresis. Any suitable process may be used, such as electrophoresis, size exclusion chromatography, or the like. In some embodiments, solid phase reversible immobilization paramagnetic beads may be employed to separate the desired DNA molecules from unattached adapters, and to select reDNAs based on size. Solid phase reversible immobilization paramagnetic beads are commercially available from Beckman Coulter (Agencourt AMPure XP), Thermofisher (MagJet), Omega Biotek (Mag-Bind), Promega Beads (Promega), and Kapa Biosystems (Kapa Pure Beads).

Before or following removal of adaptors a number of compounds and compositions may result. For example, a compound or composition that includes a plurality of adaptor-template-adaptor molecules, where the adaptor includes a restriction endonuclease site, is provided. Another composition provided herein is a population of reDNA fragments, for instance a reDNA library. In one embodiment, a composition can include population of reDNA fragments at a concentration from 1 ng/ml to 1000 ng/ml, for instance, from 10 ng/ml to 500 ng/ml, or 50 ng/ml to 150 ng/ml. In one embodiment, a composition can include population of reDNA fragments having a size range from 150 to 400 nucleotides in length, or from 150 to 300 nucleotides in length. In some embodiments the population ranges from 40, 50, 60, 70, 80, 90, 100, 110, 120, 130, 140, or 150 nucleotides to 200, 210, 220, 230, 240, 250, 260, 270, 280, 290, 300, 310, 320, 330, 340, 350, 360, 370, 380, 390, or 400 nucleotides in length.

Yet another composition provided herein is a population of reDNA fragments, for instance a reDNA library, present in an artificial biological fluid. Without intending to be limited in any way by theory, use of a population of reDNA fragments in an artificial biological fluid provides for synthetic positive and negative controls that mimic a natural test sample. The reDNA in a synthetic control has the size distribution found in natural test samples, and the genome coverage of the reDNA in a synthetic control is also similar to that found in natural test samples. The artificial biological fluid adds a further level of similarity between a natural test sample and synthetic positive and negative controls.

An artificial biological fluid is a fluid that mimics a natural biological fluid. In general, the natural biological fluid can be a fluid from which fragmented nucleic acids can be obtained from a subject. Examples include, but are not limited to, whole blood, plasma, serum, urine, saliva, sputum, lavage fluid, cerebrospinal fluid, semen, sweat, tears, saliva, stool, and the like. In general, an artificial biological fluid includes an aqueous fluid and other components of the natural fluid so the artificial fluid mimics the natural fluid. For instance, an artificial plasma can include some of the constituents of natural plasma including electrolytes, albumin, fibrinogen, clotting factors, buffer, and/or other components. Plasma is often produced by treatment of whole blood with components such as $CaCl_2$, citrate, or a combination thereof, therefore in some embodiments an artificial plasma includes $CaCl_2$, citrate, or a combination thereof. The components of biological fluids such as whole blood, plasma, serum, urine, saliva, sputum, lavage fluid, cerebrospinal fluid, semen, sweat, tears, saliva, stool, and the like are known, and can be readily recreated by the person of ordinary skill. Alternatively, artificial plasma is commercially available (ImmunoChemistry Technologies, Bloomington, Minn.). An artificial biological fluid can also include components such as, but not limited to, antimicrobial agents, stabilizers, and the like.

A population of reDNA fragments, for instance a reDNA library, can be added to an artificial biological fluid at a concentration that mimics the concentration of the fragmented nucleic acids in a natural biological sample. For instance, in an embodiment where a test sample is a blood plasma sample from a pregnant woman, the synthetic controls can be produced by adding an appropriate reDNA library to an artificial biological fluid based on a plasma sample, at a concentration that is similar to the concentration of cfDNAs in the test sample. In one embodiment, an artificial biological fluid can include a reDNA library at a concentration from 1 nanogram/milliliter (ng/ml) to 1000 ng/ml, for instance, from 10 ng/ml to 500 ng/ml, or 50 ng/ml to 150 ng/ml.

In some embodiments herein, the plurality of adaptor-template-adaptor molecules from one or more sources are then immobilized and amplified prior to sequencing (FIG. 1, block 16). Methods for attaching adaptor-template-adaptor molecules from one or more sources to a substrate are known in the art. Likewise, methods for amplifying immobilized adaptor-template-adaptor molecules include, but are not limited to, bridge amplification and kinetic exclusion amplification. Methods for immobilizing and amplifying prior to sequencing are described in, for instance, Bignell et al. (U.S. Pat. No. 8,053,192), Gunderson et al. (WO2016/130704), Shen et al. (U.S. Pat. No. 8,895,249), and Pipenburg et al. (U.S. Pat. No. 9,309,502).

A sample, including pooled samples, can then be immobilized in preparation for sequencing. Sequencing can be performed as an array of single molecules, or can be amplified prior to sequencing. The amplification can be carried out using one or more immobilized primers. The immobilized primer(s) can be a lawn on a planar surface, or on a pool of beads. The pool of beads can be isolated into an emulsion with a single bead in each "compartment" of the emulsion. At a concentration of only one template per "compartment," only a single template is amplified on each bead.

The term "solid-phase amplification" as used herein refers to any nucleic acid amplification reaction carried out on or in association with a solid support such that all or a portion of the amplified products are immobilized on the solid support as they are formed. In particular, the term encompasses solid-phase polymerase chain reaction (solid-phase PCR) and solid phase isothermal amplification which are reactions analogous to standard solution phase amplification, except that one or both of the forward and reverse amplification primers is/are immobilized on the solid support. Solid phase PCR covers systems such as emulsions, wherein one primer is anchored to a bead and the other is in free solution, and colony formation in solid phase gel matrices wherein one primer is anchored to the surface, and one is in free solution.

In some embodiments, the solid support comprises a patterned surface. A "patterned surface" refers to an arrangement of different regions in or on an exposed layer of a solid support. For example, one or more of the regions can be features where one or more universal primers are present. The features can be separated by interstitial regions where universal primers are not present. In some embodiments, the pattern can be an x-y format of features that are in rows and columns. In some embodiments, the pattern can be a repeating arrangement of features and/or interstitial regions. In some embodiments, the pattern can be a random arrangement of features and/or interstitial regions. Exemplary patterned surfaces that can be used in the methods and compositions set forth herein are described in U.S. Pat. Nos. 8,778,848, 8,778,849 and 9,079,148, and US Pub. No. 2014/0243224.

In some embodiments, the solid support comprises an array of wells or depressions in a surface. This may be fabricated as is generally known in the art using a variety of techniques, including, but not limited to, photolithography, stamping techniques, molding techniques and microetching techniques. As will be appreciated by those in the art, the technique used will depend on the composition and shape of the array substrate.

The features in a patterned surface can be wells in an array of wells (e.g. microwells or nanowells) on glass, silicon, plastic or other suitable solid supports with patterned, covalently-linked gel such as poly(N-(5-azidoacetamidylpentyl)acrylamide-co-acrylamide) (PAZAM, see, for example, US Pub. No. 2013/184796, WO 2016/066586, and WO 2015/002813). The process creates gel pads used for sequencing that can be stable over sequencing runs with a large number of cycles. The covalent linking of the polymer to the wells is helpful for maintaining the gel in the structured features throughout the lifetime of the structured substrate during a variety of uses. However in many embodiments, the gel need not be covalently linked to the wells. For example, in some conditions silane free acrylamide (SFA, see, for example, U.S. Pat. No. 8,563,477) which is not covalently attached to any part of the structured substrate, can be used as the gel material.

In particular embodiments, a structured substrate can be made by patterning a solid support material with wells (e.g. microwells or nanowells), coating the patterned support with a gel material (e.g. PAZAM, SFA or chemically modified variants thereof, such as the azidolyzed version of SFA (azido-SFA)) and polishing the gel coated support, for example via chemical or mechanical polishing, thereby retaining gel in the wells but removing or inactivating substantially all of the gel from the interstitial regions on the surface of the structured substrate between the wells. Primer nucleic acids can be attached to gel material. A solution of target nucleic acids (e.g. cfDNAs) can then be contacted with the polished substrate such that individual target nucleic acids will seed individual wells via interactions with primers attached to the gel material; however, the target nucleic acids will not occupy the interstitial regions due to absence or inactivity of the gel material. Amplification of the target nucleic acids will be confined to the wells since absence or inactivity of gel in the interstitial regions prevents outward migration of the growing nucleic acid colony. The process is conveniently manufacturable, being scalable and utilizing conventional micro- or nanofabrication methods.

Although the disclosure encompasses "solid-phase" amplification methods in which only one amplification primer is immobilized (the other primer usually being present in free solution), it is preferred for the solid support to be provided with both the forward and the reverse primers immobilized. In practice, there will be a 'plurality' of identical forward primers and/or a 'plurality' of identical reverse primers immobilized on the solid support, since the amplification process requires an excess of primers to sustain amplification. References herein to forward and reverse primers are to be interpreted accordingly as encompassing a 'plurality' of such primers unless the context indicates otherwise.

As will be appreciated by the skilled reader, any given amplification reaction requires at least one type of forward primer and at least one type of reverse primer specific for the template to be amplified. However, in certain embodiments the forward and reverse primers may comprise template-specific portions of identical sequence, and may have entirely identical nucleotide sequence and structure (including any non-nucleotide modifications). In other words, it is possible to carry out solid-phase amplification using only one type of primer, and such single-primer methods are encompassed within the scope of the disclosure. Other embodiments may use forward and reverse primers which contain identical template-specific sequences but which differ in some other structural features. For example one type of primer may contain a non-nucleotide modification which is not present in the other.

In all embodiments of the disclosure, primers for solid-phase amplification are preferably immobilized by single point covalent attachment to the solid support at or near the 5' end of the primer, leaving the template-specific portion of the primer free to anneal to its cognate template and the 3' hydroxyl group free for primer extension. Any suitable covalent attachment means known in the art may be used for this purpose. The chosen attachment chemistry will depend on the nature of the solid support, and any derivatization or functionalization applied to it. The primer itself may include a moiety, which may be a non-nucleotide chemical modification, to facilitate attachment. In a particular embodiment, the primer may include a sulphur-containing nucleophile, such as phosphorothioate or thiophosphate, at the 5' end. In the case of solid-supported polyacrylamide hydrogels, this nucleophile can bind to a bromoacetamide group present in the hydrogel. A more particular means of attaching primers and templates to a solid support is via 5' phosphorothioate attachment to a hydrogel comprised of polymerized acrylamide and N-(5-bromoacetamidylpentyl) acrylamide (BRAPA), as described fully in WO 05/065814.

Certain embodiments of the disclosure may make use of solid supports comprised of an inert substrate or matrix (e.g. glass slides, polymer beads, etc.) which has been "functionalized," for example by application of a layer or coating of an intermediate material comprising reactive groups which permit covalent attachment to biomolecules, such as polynucleotides. Examples of such supports include, but are not limited to, polyacrylamide hydrogels supported on an inert substrate such as glass. In such embodiments, the biomolecules (e.g. polynucleotides) may be directly covalently attached to the intermediate material (e.g. the hydrogel), but the intermediate material may itself be non-covalently attached to the substrate or matrix (e.g. the glass substrate). The term "covalent attachment to a solid support" is to be interpreted accordingly as encompassing this type of arrangement.

The pooled samples may be amplified on beads wherein each bead contains a forward and reverse universal primer. In a particular embodiment, the library of templates prepared according to the first, second or third aspects of the disclosure is used to prepare clustered arrays of nucleic acid colonies, analogous to those described in U.S. Pub. No. 2005/0100900, U.S. Pat. No. 7,115,400, WO 00/18957 and WO 98/44151, by solid-phase amplification and more particularly solid phase isothermal amplification. The terms "cluster" and "colony" are used interchangeably herein to refer to a discrete site on a solid support comprised of a plurality of identical immobilized nucleic acid strands and a plurality of identical immobilized complementary nucleic acid strands. The term "clustered array" refers to an array formed from such clusters or colonies. In this context the term "array" is not to be understood as requiring an ordered arrangement of clusters.

The term "solid phase," or "surface," is used to mean either a planar array wherein primers are attached to a flat surface, for example, glass, silica or plastic microscope slides or similar flow cell devices; beads, wherein either one or two primers are attached to the beads and the beads are amplified; or an array of beads on a surface after the beads have been amplified.

Clustered arrays can be prepared using either a process of thermocycling, as described in WO 98/44151, or a process whereby the temperature is maintained as a constant, and the cycles of extension and denaturing are performed using changes of reagents. Such isothermal amplification methods are described in patent application numbers WO 02/46456 and U.S. Pub. No. 2008/0009420. Due to the lower temperatures required in the isothermal process, this is particularly preferred.

It will be appreciated that any of the amplification methodologies described herein or generally known in the art may be used with universal or target-specific primers to amplify immobilized DNA fragments. Suitable methods for amplification include, but are not limited to, the polymerase chain reaction (PCR), strand displacement amplification (SDA), transcription mediated amplification (TMA) and nucleic acid sequence based amplification (NASBA), as described in U.S. Pat. No. 8,003,354. The above amplification methods may be employed to amplify one or more nucleic acids of interest. For example, PCR, including multiplex PCR, SDA, TMA, NASBA and the like may be used to amplify immobilized DNA fragments. In some embodiments, primers directed specifically to the polynucleotide of interest are included in the amplification reaction.

Other suitable methods for amplification of polynucleotides may include oligonucleotide extension and ligation, rolling circle amplification (RCA) (Lizardi et al., Nat. Genet. 19:225-232 (1998)) and oligonucleotide ligation assay (OLA) (See generally U.S. Pat. Nos. 7,582,420, 5,185,243, 5,679,524 and 5,573,907; EP 0 320 308 B1; EP 0 336 731 B1; EP 0 439 182 B1; WO 90/01069; WO 89/12696; and WO 89/09835) technologies. It will be appreciated that these amplification methodologies may be designed to amplify immobilized DNA fragments. For example, in some embodiments, the amplification method may include ligation probe amplification or oligonucleotide ligation assay (OLA) reactions that contain primers directed specifically to the nucleic acid of interest. In some embodiments, the amplification method may include a primer extension-ligation reaction that contains primers directed specifically to the nucleic acid of interest. As a non-limiting example of primer extension and ligation primers that may be specifically designed to amplify a nucleic acid of interest, the amplification may include primers used for the GoldenGate assay (Illumina, Inc., San Diego, Calif.) as exemplified by U.S. Pat. Nos. 7,582,420 and 7,611,869.

Exemplary isothermal amplification methods that may be used in a method of the present disclosure include, but are not limited to, Multiple Displacement Amplification (MDA) as exemplified by, for example Dean et al., Proc. Natl. Acad. Sci. USA 99:5261-66 (2002) or isothermal strand displacement nucleic acid amplification exemplified by, for example U.S. Pat. No. 6,214,587. Other non-PCR-based methods that may be used in the present disclosure include, for example, strand displacement amplification (SDA) which is described in, for example Walker et al., Molecular Methods for Virus Detection, Academic Press, Inc., 1995; U.S. Pat. Nos. 5,455,166, and 5,130,238, and Walker et al., Nucl. Acids Res. 20:1691-96 (1992) or hyper-branched strand displacement amplification which is described in, for example Lage et al., Genome Res. 13:294-307 (2003). Isothermal amplification methods may be used with the strand-displacing Phi 29 polymerase or Bst DNA polymerase large fragment, 5'->3' exo- for random primer amplification of genomic DNA. The use of these polymerases takes advantage of their high processivity and strand displacing activity. High processivity allows the polymerases to produce fragments that are 10-20 kb in length. As set forth above, smaller fragments may be produced under isothermal conditions using polymerases having low processivity and strand-displacing activity such as Klenow polymerase. Additional description of amplification reactions, conditions and components are set forth in detail in the disclosure of U.S. Pat. No. 7,670,810.

Another polynucleotide amplification method that is useful in the present disclosure is Tagged PCR which uses a population of two-domain primers having a constant 5' region followed by a random 3' region as described, for example, in Grothues et al. Nucleic Acids Res. 21(5):1321-2 (1993). The first rounds of amplification are carried out to allow a multitude of initiations on heat denatured DNA based on individual hybridization from the randomly-synthesized 3' region. Due to the nature of the 3' region, the sites of initiation are contemplated to be random throughout the genome. Thereafter, the unbound primers may be removed and further replication may take place using primers complementary to the constant 5' region.

In some embodiments, isothermal amplification can be performed using kinetic exclusion amplification (KEA), also referred to as exclusion amplification (ExAmp). A nucleic acid library of the present disclosure can be made using a method that includes a step of reacting an amplification reagent to produce a plurality of amplification sites that each includes a substantially clonal population of amplicons from an individual target nucleic acid that has seeded the site. In some embodiments the amplification reaction proceeds until a sufficient number of amplicons are generated to fill the capacity of the respective amplification site. Filling an already seeded site to capacity in this way inhibits target nucleic acids from landing and amplifying at the site thereby producing a clonal population of amplicons at the site. In some embodiments, apparent clonality can be achieved even if an amplification site is not filled to capacity prior to a second target nucleic acid arriving at the site. Under some conditions, amplification of a first target nucleic acid can proceed to a point that a sufficient number of copies are made to effectively outcompete or overwhelm production of copies from a second target nucleic acid that is transported to the site. For example in an embodiment that uses a bridge amplification process on a circular feature that is smaller than 500 nm in diameter, it has been determined that after 14 cycles of exponential amplification for a first target nucleic acid, contamination from a second target nucleic acid at the same site will produce an insufficient number of contaminating amplicons to adversely impact sequencing-by-synthesis analysis on an Illumina sequencing platform.

Amplification sites in an array can be, but need not be, entirely clonal in particular embodiments. Rather, for some applications, an individual amplification site can be predominantly populated with amplicons from a first target nucleic acid and can also have a low level of contaminating amplicons from a second target nucleic acid. An array can have one or more amplification sites that have a low level of contaminating amplicons so long as the level of contamination does not have an unacceptable impact on a subsequent use of the array. For example, when the array is to be used in a detection application, an acceptable level of contamination would be a level that does not impact signal to noise or resolution of the detection technique in an unacceptable way. Accordingly, apparent clonality will generally be relevant to a particular use or application of an array made by the methods set forth herein. Exemplary levels of contamination that can be acceptable at an individual amplification site for particular applications include, but are not limited to, at most 0.1%, 0.5%, 1%, 5%, 10% or 25% contaminating amplicons. An array can include one or more amplification sites having these exemplary levels of contaminating amplicons. For example, up to 5%, 10%, 25%, 50%, 75%, or even 100% of the amplification sites in an array can have some contaminating amplicons. It will be understood that in an array or other collection of sites, at least 50%, 75%, 80%, 85%, 90%, 95% or 99% or more of the sites can be clonal or apparently clonal.

In some embodiments, kinetic exclusion can occur when a process occurs at a sufficiently rapid rate to effectively exclude another event or process from occurring. Take for example the making of a nucleic acid array where sites of the array are randomly seeded with target nucleic acids from a solution and copies of the target nucleic acid are generated in an amplification process to fill each of the seeded sites to capacity. In accordance with the kinetic exclusion methods of the present disclosure, the seeding and amplification processes can proceed simultaneously under conditions where the amplification rate exceeds the seeding rate. As such, the relatively rapid rate at which copies are made at a site that has been seeded by a first target nucleic acid will effectively exclude a second nucleic acid from seeding the site for amplification. Kinetic exclusion amplification methods can be performed as described in detail in the disclosure of US Application Pub. No. 2013/0338042.

Kinetic exclusion can exploit a relatively slow rate for initiating amplification (e.g. a slow rate of making a first copy of a target nucleic acid) vs. a relatively rapid rate for making subsequent copies of the target nucleic acid (or of the first copy of the target nucleic acid). In one exemplary embodiment, kinetic exclusion occurs due to the relatively slow rate of target nucleic acid seeding (e.g. relatively slow diffusion or transport) vs. the relatively rapid rate at which amplification occurs to fill the site with copies of the nucleic acid seed. In another exemplary embodiment, kinetic exclusion can occur due to a delay in the formation of a first copy of a target nucleic acid that has seeded a site (e.g. delayed or slow activation) vs. the relatively rapid rate at which subsequent copies are made to fill the site. In this example, an individual site may have been seeded with several different target nucleic acids (e.g. several target nucleic acids can be present at each site prior to amplification). However, first copy formation for any given target nucleic acid can be activated randomly such that the average rate of first copy formation is relatively slow compared to the rate at which subsequent copies are generated. In this case, although an individual site may have been seeded with several different target nucleic acids, kinetic exclusion will allow only one of those target nucleic acids to be amplified. More specifically, once a first target nucleic acid has been activated for amplification, the site will rapidly fill to capacity with its copies, thereby preventing copies of a second target nucleic acid from being made at the site.

An amplification reagent can include further components that facilitate amplicon formation and in some cases increase the rate of amplicon formation. An example is a recombinase. Recombinase can facilitate amplicon formation by allowing repeated invasion/extension. More specifically, recombinase can facilitate invasion of a target nucleic acid by the polymerase and extension of a primer by the polymerase using the target nucleic acid as a template for amplicon formation. This process can be repeated as a chain reaction where amplicons produced from each round of invasion/extension serve as templates in a subsequent round. The process can occur more rapidly than standard PCR since a denaturation cycle (e.g. via heating or chemical denaturation) is not required. As such, recombinase-facilitated amplification can be carried out isothermally. It is generally desirable to include ATP, or other nucleotides (or in some cases non-hydrolyzable analogs thereof) in a recombinase-facilitated amplification reagent to facilitate amplification. A mixture of recombinase and single stranded binding (SSB) protein is particularly useful as SSB can further facilitate amplification. Exemplary formulations for recombinase-facilitated amplification include those sold commercially as TwistAmp kits by TwistDx (Cambridge, UK). Useful components of recombinase-facilitated amplification reagent and reaction conditions are set forth in U.S. Pat. Nos. 5,223,414 and 7,399,590.

Another example of a component that can be included in an amplification reagent to facilitate amplicon formation and in some cases to increase the rate of amplicon formation is a helicase. Helicase can facilitate amplicon formation by allowing a chain reaction of amplicon formation. The process can occur more rapidly than standard PCR since a denaturation cycle (e.g. via heating or chemical denaturation) is not required. As such, helicase-facilitated amplification can be carried out isothermally. A mixture of helicase and single stranded binding (SSB) protein is particularly useful as SSB can further facilitate amplification. Exemplary formulations for helicase-facilitated amplification include those sold commercially as IsoAmp kits from Biohelix (Beverly, Mass.). Further, examples of useful formulations that include a helicase protein are described in U.S. Pat. Nos. 7,399,590 and 7,829,284.

Yet another example of a component that can be included in an amplification reagent to facilitate amplicon formation and in some cases increase the rate of amplicon formation is an origin binding protein.

Following attachment of adaptor-template-adaptor molecules to a surface, the sequence at least a portion of the immobilized and amplified adaptor-template-adaptor molecules is determined. Sequencing can be carried out using any suitable sequencing technique, and methods for determining the sequence of immobilized and amplified adaptor-template-adaptor molecules, including strand re-synthesis, are known in the art and are described in, for instance, Bignell et al. (U.S. Pat. No. 8,053,192), Gunderson et al. (WO2016/130704), Shen et al. (U.S. Pat. No. 8,895,249), and Pipenburg et al. (U.S. Pat. No. 9,309,502).

The methods described herein can be used in conjunction with a variety of nucleic acid sequencing techniques, also referred to as nucleic acid detection tests. Particularly applicable techniques are those wherein nucleic acids are attached at fixed locations in an array such that their relative positions do not change and wherein the array is repeatedly imaged. Embodiments in which images are obtained in different color channels, for example, coinciding with different labels used to distinguish one nucleotide base type from another are particularly applicable. In some embodiments, the process to determine the nucleotide sequence of a target nucleic acid can be an automated process. Preferred embodiments include sequencing-by-synthesis ("SBS") techniques. The nucleic acid sequencing techniques can also be used for microarray analysis.

SBS techniques generally involve the enzymatic extension of a nascent nucleic acid strand through the iterative addition of nucleotides against a template strand. In traditional methods of SBS, a single nucleotide monomer may be provided to a target nucleotide in the presence of a polymerase in each delivery. However, in the methods described herein, more than one type of nucleotide monomer can be provided to a target nucleic acid in the presence of a polymerase in a delivery.

SBS can use nucleotide monomers that have a terminator moiety or those that lack any terminator moieties. Methods utilizing nucleotide monomers lacking terminators include, for example, pyrosequencing and sequencing using γ-phosphate-labeled nucleotides, as set forth in further detail herein. In methods using nucleotide monomers lacking terminators, the number of nucleotides added in each cycle is generally variable and dependent upon the template sequence and the mode of nucleotide delivery. For SBS techniques that use nucleotide monomers having a terminator moiety, the terminator can be effectively irreversible under the sequencing conditions used as is the case for traditional Sanger sequencing which uses dideoxynucleotides, or the terminator can be reversible as is the case for sequencing methods developed by Solexa (now Illumina, Inc.).

SBS techniques can use nucleotide monomers that have a label moiety or those that lack a label moiety. Accordingly, incorporation events can be detected based on a characteristic of the label, such as fluorescence of the label; a characteristic of the nucleotide monomer such as molecular weight or charge; a byproduct of incorporation of the nucleotide, such as release of pyrophosphate; or the like. In embodiments where two or more different nucleotides are present in a sequencing reagent, the different nucleotides can be distinguishable from each other, or alternatively, the two or more different labels can be the indistinguishable under the detection techniques being used. For example, the different nucleotides present in a sequencing reagent can have different labels and they can be distinguished using appropriate optics as exemplified by the sequencing methods developed by Solexa (now Illumina, Inc.).

Preferred embodiments include pyrosequencing techniques. Pyrosequencing detects the release of inorganic pyrophosphate (PPi) as particular nucleotides are incorporated into the nascent strand (Ronaghi, M., Karamohamed, S., Pettersson, B., Uhlen, M. and Nyren, P. (1996) "Real-time DNA sequencing using detection of pyrophosphate release." Analytical Biochemistry 242(1), 84-9; Ronaghi, M. (2001) "Pyrosequencing sheds light on DNA sequencing." Genome Res. 11(1), 3-11; Ronaghi, M., Uhlen, M. and Nyren, P. (1998) "A sequencing method based on real-time pyrophosphate." Science 281(5375), 363; U.S. Pat. Nos. 6,210,891; 6,258,568 and 6,274,320). In pyrosequencing, released PPi can be detected by being immediately converted to adenosine triphosphate (ATP) by ATP sulfurase, and the level of ATP generated is detected via luciferase-produced photons. The nucleic acids to be sequenced can be attached to features in an array and the array can be imaged to capture the chemiluminescent signals that are produced due to incorporation of a nucleotides at the features of the array. An image can be obtained after the array is treated with a particular nucleotide type (e.g. A, T, C or G). Images obtained after addition of each nucleotide type will differ with regard to which features in the array are detected. These differences in the image reflect the different sequence content of the features on the array. However, the relative locations of each feature will remain unchanged in the images. The images can be stored, processed and analyzed using the methods set forth herein. For example, images obtained after treatment of the array with each different nucleotide type can be handled in the same way as exemplified herein for images obtained from different detection channels for reversible terminator-based sequencing methods.

In another exemplary type of SBS, cycle sequencing is accomplished by stepwise addition of reversible terminator nucleotides containing, for example, a cleavable or photobleachable dye label as described, for example, in WO 04/018497 and U.S. Pat. No. 7,057,026. This approach is being commercialized by Solexa (now Illumina Inc.), and is also described in WO 91/06678 and WO 07/123,744. The availability of fluorescently-labeled terminators in which both the termination can be reversed and the fluorescent label cleaved facilitates efficient cyclic reversible termination (CRT) sequencing. Polymerases can also be co-engineered to efficiently incorporate and extend from these modified nucleotides.

Preferably in reversible terminator-based sequencing embodiments, the labels do not substantially inhibit extension under SBS reaction conditions. However, the detection labels can be removable, for example, by cleavage or degradation. Images can be captured following incorporation of labels into arrayed nucleic acid features. In particular embodiments, each cycle involves simultaneous delivery of four different nucleotide types to the array and each nucleotide type has a spectrally distinct label. Four images can then be obtained, each using a detection channel that is selective for one of the four different labels. Alternatively, different nucleotide types can be added sequentially and an image of the array can be obtained between each addition step. In such embodiments each image will show nucleic acid features that have incorporated nucleotides of a particular type. Different features will be present or absent in the different images due the different sequence content of each feature. However, the relative position of the features will remain unchanged in the images. Images obtained from such reversible terminator-SBS methods can be stored, processed and analyzed as set forth herein. Following the image capture step, labels can be removed and reversible terminator moieties can be removed for subsequent cycles of nucleotide addition and detection. Removal of the labels after they have been detected in a particular cycle and prior to a subsequent cycle can provide the advantage of reducing background signal and crosstalk between cycles. Examples of useful labels and removal methods are set forth herein.

In particular embodiments some or all of the nucleotide monomers can include reversible terminators. In such embodiments, reversible terminators/cleavable fluorophores can include fluorophores linked to the ribose moiety via a 3' ester linkage (Metzker, Genome Res. 15:1767-1776 (2005)). Other approaches have separated the terminator chemistry from the cleavage of the fluorescence label (Ruparel et al., Proc Natl Acad Sci USA 102: 5932-7 (2005)). Ruparel et al. described the development of reversible terminators that used a small 3' allyl group to block extension, but could easily be deblocked by a short treatment with a palladium catalyst. The fluorophore was attached to the base via a photocleavable linker that could easily be cleaved by a 30 second exposure to long wavelength UV light. Thus, either disulfide reduction or photocleavage can be used as a cleavable linker. Another approach to reversible termination is the use of natural termination that ensues after placement of a bulky dye on a dNTP. The presence of a charged bulky dye on the dNTP can act as an effective terminator through steric and/or electrostatic hindrance. The presence of one incorporation event prevents further incorporations unless the dye is removed. Cleavage of the dye removes the fluorophore and effectively reverses the termination. Examples of modified nucleotides are also described in U.S. Pat. Nos. 7,427,673, and 7,057,026.

Additional exemplary SBS systems and methods which can be used with the methods and systems described herein are described in U.S. Pub. Nos. 2007/0166705, 2006/0188901, 2006/0240439, 2006/0281109, 2012/0270305, and 2013/0260372, U.S. Pat. No. 7,057,026, PCT Publication No. WO 05/065814, U.S. Patent Application Publication No. 2005/0100900, and PCT Publication Nos. WO 06/064199 and WO 07/010,251.

Some embodiments can use detection of four different nucleotides using fewer than four different labels. For example, SBS can be performed utilizing methods and systems described in the incorporated materials of U.S. Pub. No. 2013/0079232. As a first example, a pair of nucleotide types can be detected at the same wavelength, but distinguished based on a difference in intensity for one member of the pair compared to the other, or based on a change to one member of the pair (e.g. via chemical modification, photochemical modification or physical modification) that causes apparent signal to appear or disappear compared to the signal detected for the other member of the pair. As a second example, three of four different nucleotide types can be detected under particular conditions while a fourth nucleotide type lacks a label that is detectable under those conditions, or is minimally detected under those conditions (e.g., minimal detection due to background fluorescence, etc.). Incorporation of the first three nucleotide types into a nucleic acid can be determined based on presence of their respective signals and incorporation of the fourth nucleotide type into the nucleic acid can be determined based on absence or minimal detection of any signal. As a third example, one nucleotide type can include label(s) that are detected in two different channels, whereas other nucleotide types are detected in no more than one of the channels. The aforementioned three exemplary configurations are not considered mutually exclusive and can be used in various combinations. An exemplary embodiment that combines all three examples, is a fluorescent-based SBS method that uses a first nucleotide type that is detected in a first channel (e.g. dATP having a label that is detected in the first channel when excited by a first excitation wavelength), a second nucleotide type that is detected in a second channel (e.g. dCTP having a label that is detected in the second channel when excited by a second excitation wavelength), a third nucleotide type that is detected in both the first and the second channel (e.g. dTTP having at least one label that is detected in both channels when excited by the first and/or second excitation wavelength) and a fourth nucleotide type that lacks a label that is not, or minimally, detected in either channel (e.g. dGTP having no label).

Further, as described in the incorporated materials of U.S. Pub. No. 2013/0079232, sequencing data can be obtained using a single channel. In such so-called one-dye sequencing approaches, the first nucleotide type is labeled but the label is removed after the first image is generated, and the second nucleotide type is labeled only after a first image is generated. The third nucleotide type retains its label in both the first and second images, and the fourth nucleotide type remains unlabeled in both images.

Some embodiments can use sequencing by ligation techniques. Such techniques use DNA ligase to incorporate oligonucleotides and identify the incorporation of such oligonucleotides. The oligonucleotides typically have different labels that are correlated with the identity of a particular nucleotide in a sequence to which the oligonucleotides hybridize. As with other SBS methods, images can be obtained following treatment of an array of nucleic acid features with the labeled sequencing reagents. Each image will show nucleic acid features that have incorporated labels of a particular type. Different features will be present or absent in the different images due the different sequence content of each feature, but the relative position of the features will remain unchanged in the images. Images obtained from ligation-based sequencing methods can be stored, processed and analyzed as set forth herein. Exemplary SBS systems and methods which can be used with the methods and systems described herein are described in U.S. Pat. Nos. 6,969,488, 6,172,218, and 6,306,597.

Some embodiments can use nanopore sequencing (Deamer, D. W. & Akeson, M. "Nanopores and nucleic acids: prospects for ultrarapid sequencing." Trends Biotechnol. 18, 147-151 (2000); Deamer, D. and D. Branton, "Characterization of nucleic acids by nanopore analysis," Acc. Chem. Res. 35:817-825 (2002); Li, J., M. Gershow, D. Stein, E. Brandin, and J. A. Golovchenko, "DNA molecules and configurations in a solid-state nanopore microscope" Nat. Mater. 2:611-615 (2003)). In such embodiments, the target nucleic acid passes through a nanopore. The nanopore can be a synthetic pore or biological membrane protein, such as α-hemolysin. As the target nucleic acid passes through the nanopore, each base-pair can be identified by measuring fluctuations in the electrical conductance of the pore. (U.S. Pat. No. 7,001,792; Soni, G. V. & Meller, "A. Progress toward ultrafast DNA sequencing using solid-state nanopores." Clin. Chem. 53, 1996-2001 (2007); Healy, K. "Nanopore-based single-molecule DNA analysis." Nanomed. 2, 459-481 (2007); Cockroft, S. L., Chu, J., Amorin, M. & Ghadiri, M. R. "A single-molecule nanopore device detects DNA polymerase activity with single-nucleotide resolution." J. Am. Chem. Soc. 130, 818-820 (2008)). Data obtained from nanopore sequencing can be stored, processed and analyzed as set forth herein. In particular, the data can be treated as an image in accordance with the exemplary treatment of optical images and other images that is set forth herein.

Some embodiments can use methods involving the real-time monitoring of DNA polymerase activity. Nucleotide incorporations can be detected through fluorescence resonance energy transfer (FRET) interactions between a fluorophore-bearing polymerase and γ-phosphate-labeled nucleotides as described, for example, in U.S. Pat. Nos. 7,329,492 and 7,211,414, or nucleotide incorporations can be detected with zero-mode waveguides as described, for example, in U.S. Pat. No. 7,315,019, and using fluorescent nucleotide analogs and engineered polymerases as described, for example, in U.S. Pat. No. 7,405,281 and U.S. Pub. No. 2008/0108082. The illumination can be restricted to a zeptoliter-scale volume around a surface-tethered polymerase such that incorporation of fluorescently labeled nucleotides can be observed with low background (Levene, M. J. et al. "Zero-mode waveguides for single-molecule analysis at high concentrations." Science 299, 682-686 (2003); Lundquist, P. M. et al. "Parallel confocal detection of single molecules in real time." Opt. Lett. 33, 1026-1028 (2008); Korlach, J. et al. "Selective aluminum passivation for targeted immobilization of single DNA polymerase molecules in zero-mode waveguide nano structures." Proc. Natl. Acad. Sci. USA 105, 1176-1181 (2008)). Images obtained from such methods can be stored, processed and analyzed as set forth herein.

Some SBS embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in U.S. Pub. Nos. 2009/0026082; 2009/0127589; 2010/0137143; and 2010/0282617. Methods set forth herein for amplifying target nucleic acids using kinetic exclusion can be readily applied to substrates used for detecting protons. More specifically, methods set forth herein can be used to produce clonal populations of amplicons that are used to detect protons.

The above SBS methods can be advantageously carried out in multiplex formats such that multiple different target nucleic acids are manipulated simultaneously. In particular embodiments, different target nucleic acids can be treated in a common reaction vessel or on a surface of a particular substrate. This allows convenient delivery of sequencing reagents, removal of unreacted reagents and detection of incorporation events in a multiplex manner. In embodiments using surface-bound target nucleic acids, the target nucleic acids can be in an array format. In an array format, the target nucleic acids can be typically bound to a surface in a spatially distinguishable manner. The target nucleic acids can be bound by direct covalent attachment, attachment to a bead or other particle or binding to a polymerase or other molecule that is attached to the surface. The array can include a single copy of a target nucleic acid at each site (also referred to as a feature) or multiple copies having the same sequence can be present at each site or feature. Multiple copies can be produced by amplification methods such as, bridge amplification or emulsion PCR as described in further detail below.

The methods set forth herein can use arrays having features at any of a variety of densities including, for example, at least about 10 features/cm2, 100 features/cm2, 500 features/cm2, 1,000 features/cm2, 5,000 features/cm2, 10,000 features/cm2, 50,000 features/cm2, 100,000 features/cm2, 1,000,000 features/cm2, 5,000,000 features/cm2, or higher.

An advantage of the methods set forth herein is that they provide for rapid and efficient detection of a plurality of target nucleic acid in parallel. Accordingly the present disclosure provides integrated systems capable of preparing and detecting nucleic acids using techniques known in the art such as those exemplified above. Thus, an integrated system of the present disclosure can include fluidic components capable of delivering amplification reagents and/or sequencing reagents to one or more immobilized DNA fragments, the system comprising components such as pumps, valves, reservoirs, fluidic lines and the like. A flow cell can be configured and/or used in an integrated system for detection of target nucleic acids. Exemplary flow cells are described, for example, in U.S. Pub. No. 2010/0111768 and U.S. Ser. No. 13/273,666. As exemplified for flow cells, one or more of the fluidic components of an integrated system can be used for an amplification method and for a detection method. Taking a nucleic acid sequencing embodiment as an example, one or more of the fluidic components of an integrated system can be used for an amplification method set forth herein and for the delivery of sequencing reagents in a sequencing method such as those exemplified above. Alternatively, an integrated system can include separate fluidic systems to carry out amplification methods and to carry out detection methods. Examples of integrated sequencing systems that are capable of creating amplified nucleic acids and also determining the sequence of the nucleic acids include, without limitation, the MiSeq™ platform (Illumina, Inc., San Diego, Calif.) and devices described in U.S. Ser. No. 13/273,666.

The reDNAs described herein are useful as controls in a variety of applications. For example, the reDNAs can be sequenced using any suitable sequencing technique known in the art. A composition of reDNAs can have any number of known characteristics, such as known chromosomal copy number, known G/C content, known distribution of sequences across chromosomes and/or a genome, or other known properties, and as such, the compositions presented herein can be used as controls in sequencing methods to account for changes in experimental conditions. As an example, if a reDNA library is known to have a certain G/C content, the library can be included in a multiplex sequencing run to identify if any sequencing analysis produces any deviance from the expected G/C content.

In some embodiments, the reDNA compositions can be a control for quality of library preparation methods. For example, preparation of a sequencing library can include a variety of steps, including DNA end repair, A-tailing, ligation of adaptors, and/or amplification steps. Where any of these steps produce a bias towards any characteristic, such as distribution across a genome or chromosome, type of sequence, G/C content, length of fragment, and the like, the bias can be detected in downstream analysis, such as sequencing analysis.

In some embodiments, the reDNA compositions can be a control for a sequencing instrument. Similarly, the reDNA compositions can be a control for an array instrument. For example, a sequencing instrument or array instrument may perform a variety of functions, including fluid transfer for washing, nucleotide incorporation, amplification, scanning, chemical steps such as cleavage reactions, solid-phase amplification, heating/cooling, production of excitation light, detection of fluorescent emission signals, movement of cameras and stages, and scanning of microscopic features on a solid support. Where any of these steps produce a bias towards any characteristic, such as distribution across a genome or chromosome, type of sequence, G/C content, length of fragment, and the like, the bias can be detected in downstream analysis, such as sequencing analysis or array analysis. The instrument can be calibrated to adjust or correct any process, condition or component that is causing bias or malfunction.

In some embodiments, the reDNA compositions can be a validation control for a nucleic acid sequencing test. For example, sequencing-based tests can detect one or more genetic abnormalities, such as SNP variants, aneuploidies, insertions, deletions, repeat expansions, rearrangements, and the like. In some embodiments, a reDNA composition is used as a validation control for a sequencing-based noninvasive prenatal test. In some embodiments, a reDNA composition is used as a validation control for sequencing-based tumor detection test. In an example of such an embodiment, where a test is being developed for a rare abnormality, it may be difficult to obtain enough biological samples to perform the large number of validation tests to ensure the sensitivity and/or specificity of the test. Thus, a reDNA composition derived from, for instance, cfDNA obtained from an individual harboring the rare abnormality, can be useful because it can be created in large enough quantities to allow for many, or unlimited repeat runs of the test during validation studies.

In some embodiments, a reDNA composition is used as a validation control for a sequencing-based companion diagnostic test. Companion diagnostic tests are useful to determine if an individual has a genetic characteristic that qualifies the individual as a candidate for a therapeutic treatment. In some embodiments, the companion diagnostic test determines the presence or identity of genetic variants in a sample in order to determine whether a therapeutic treatment will be suitable in a treatment regimen. In such embodiments, the diagnostic test may need to be validated a number of times to ensure the test is repeatable and has the desired sensitivity and/or specificity. Thus, a reDNA composition derived from, for instance, cfDNA obtained from an individual harboring the genetic characteristic, can be useful because it can be created in large enough quantities to allow for many, or unlimited repeat runs of the test during validation studies.

EXEMPLARY EMBODIMENTS

Embodiment 1

A method comprising:
providing a sample of a plurality of double-stranded template nucleic acids obtained from a subject;

ligating a universal adaptor to both ends of the template nucleic acids to form a plurality of adaptor-template-adaptor molecules, wherein each of the plurality of adaptor-template-adaptor molecules comprises a template nucleic acid flanked by the universal adaptor, wherein the universal adaptor comprises a region of double stranded nucleic acid; and amplifying the plurality of adaptor-template-adaptor molecules with a first universal primer and a second universal primer to result in amplified adaptor-template-adaptor molecules;

removing the universal adaptor from both ends of the amplified adaptor-template-adaptor molecules to result in unattached universal adaptors and a plurality of regenerated template nucleic acids (reDNAs).

Embodiment 2

The method of Embodiment 1 wherein the double-stranded template nucleic acids are DNA.

Embodiment 3

The method of any one of Embodiments 1-2 wherein the double-stranded template nucleic acids are cell free DNA (cfDNA).

Embodiment 4

The method of any one of Embodiments 1-3 wherein the subject is a pregnant human, and wherein the double-stranded template nucleic acids comprise a mixture of fetal and maternal nucleic acids.

Embodiment 5

The method of any one of Embodiments 1-4 wherein the sample comprises cfDNA.

Embodiment 6

The method of any one of Embodiments 1-5 wherein the fetus does not comprise a genetic condition.

Embodiment 7

The method of any one of Embodiments 1-6 wherein the fetus comprises a genetic condition.

Embodiment 8

The method of any one of Embodiments 1-7 wherein the genetic condition is an aneuploidy.

Embodiment 9

The method of any one of Embodiments 1-8 wherein the aneuploidy is a trisomy.

Embodiment 10

The method of any one of Embodiments 1-9 wherein the trisomy is Trisomy 21, Trisomy 18, Trisomy 13, Trisomy 9, Trisomy 8, Trisomy 22, XXX, XXY, or XYY.

Embodiment 11

The method of any one of Embodiments 1-10 wherein the genetic condition comprises an under-representation of a nucleotide sequence.

Embodiment 12

The method of any one of Embodiments 1-11 wherein the subject is suspected of having a neoplasm.

Embodiment 13

The method of any one of Embodiments 1-12 wherein the sample comprises circulating tumor DNA and cell free normal DNA.

Embodiment 14

The method of any one of Embodiments 1-13 wherein the sample comprises blood, urine, sputum, or stool.

Embodiment 15

The method of any one of Embodiments 1-14 further comprising treating, before the ligating, the plurality of double-stranded template nucleic acids to modify ends to be blunt ended.

Embodiment 16

The method of any one of Embodiments 1-15 further comprising treating, before the ligating, the plurality of double-stranded template nucleic acids to modify 3' ends to terminate as a 3' overhang structure.

Embodiment 17

The method of any one of Embodiments 1-16 wherein the universal adaptor further comprises a region of single-stranded non-complementary nucleic acid strands comprising at least one universal primer binding site, and wherein the ligating covalently attaches the region of double stranded nucleic acid of the universal adaptor to each end of the template nucleic acids.

Embodiment 18

The method of any one of Embodiments 1-17 wherein the amplifying comprises an exponential amplification reaction.

Embodiment 19

The method of any one of Embodiments 1-18 wherein the exponential amplification reaction comprises a polymerase chain reaction (PCR).

Embodiment 20

The method of any one of Embodiments 1-19 wherein the amplifying comprises a DNA polymerase with a low error rate.

Embodiment 21

The method of any one of Embodiments 1-20 wherein the universal adaptor comprises a restriction endonuclease recognition site, and the removing comprises exposing the amplified adaptor-template-adaptor molecules to a restriction endonuclease and cleaving the adaptor-template-adaptor molecules to result in removed universal adaptors and a plurality of reDNAs.

Embodiment 22

The method of any one of Embodiments 1-21 wherein the cleavage site and the recognition site of the restriction endonuclease are separate.

Embodiment 23

The method of any one of Embodiments 1-22 wherein the restriction endonuclease is SapI, MlyI, or BpuEI.

Embodiment 24

The method of any one of Embodiments 1-23 wherein the reDNAs retain a portion of the universal adaptor at each end of the template.

Embodiment 25

The method of any one of Embodiments 1-24 wherein the first universal primer and the second universal primer comprise a capture agent.

Embodiment 26

The method of any one of Embodiments 1-25 wherein the capture agent comprises biotin.

Embodiment 27

The method of any one of Embodiments 1-26 wherein the universal adaptor comprises a restriction endonuclease recognition site, wherein the removing comprises contacting the adaptor-template-adaptor molecules with a surface comprising a compound that binds the ligand to result in bound amplified adaptor-template-adaptor molecules, and exposing the bound amplified adaptor-template-adaptor molecules to a restriction endonuclease that cleaves the bound amplified adaptor-template-adaptor molecules to result in removed universal adaptors and a plurality of reDNAs, wherein the removed universal adaptors are bound to the surface.

Embodiment 28

The method of any one of Embodiments 1-27 wherein the removing further comprises separating the removed universal adaptors from the reDNAs.

Embodiment 29

The method of any one of Embodiments 1-28 wherein the separating comprises contacting a mixture comprising the removed universal adaptors and the reDNAs with a compound that binds the ligand, wherein the compound is attached to a surface, and wherein the removed universal adaptors are bound to the surface.

Embodiment 30

The method of any one of Embodiments 1-29 wherein the surface comprises a bead.

Embodiment 31

The method of any one of Embodiments 1-30 further comprising removing the surface comprising the bound removed universal adaptors to result in separation of the removed universal adaptors from the reDNAs.

Embodiment 32

The method of any one of Embodiments 1-31 wherein the removing comprises selection of reDNAs that fall within a predetermined size range.

Embodiment 33

A method, comprising:
providing a plurality of regenerated template nucleic acids (reDNAs) originating from a sample obtained from one subject,
    wherein each reDNA is a template;
ligating a universal adaptor to both ends of the template nucleic acids to form a plurality of adaptor-template-adaptor molecules,
wherein each of the plurality of adaptor-template-adaptor molecules comprises a template nucleic acid flanked by the universal adaptor,
wherein the universal adapter comprises (i) a region of double stranded nucleic acid, and (ii) a region of single-stranded non-complementary nucleic acid strands comprising at least one universal primer binding site,
thereby producing a sequencing library for determining the sequence of at least a portion of templates.

Embodiment 34

The method of Embodiment 33, wherein the region of single-stranded non-complementary nucleic acid strands further comprises at least one universal extension primer binding site.

Embodiment 35

The method of any one of Embodiments 33-34, wherein the region of double stranded nucleic acid distal to the region of single-stranded non-complementary nucleic acid strands terminates as a blunt end structure.

Embodiment 36

The method of any one of Embodiments 33-35, wherein the plurality of templates comprise blunt end structures.

Embodiment 37

The method of any one of Embodiments 33-36, wherein the region of double stranded nucleic acid distal to the region of single-stranded non-complementary nucleic acid strands terminates as a 3' overhang structure.

Embodiment 38

The method of any one of Embodiments 33-37, wherein the 3' overhang structure comprises an overhang structure of 1 to 4 nucleotides.

Embodiment 39

The method of any one of Embodiments 33-38, wherein the 3' overhang structure comprises an overhang of a T nucleotide.

Embodiment 40

The method of any one of Embodiments 33-39, wherein the templates comprise a 3' overhang structure complementary to the 3' overhang structure of the region of double stranded nucleic acid.

Embodiment 41

The method of any one of Embodiments 33-40, further comprising:
  providing a surface comprising a plurality of amplification sites,
  wherein the amplification sites comprise at least two populations of attached single stranded nuclei acids having a free 3' end, and
  contacting the surface comprising amplification sites with the plurality of adaptor-template-adaptor molecules under conditions suitable to produce a plurality of amplification sites that each comprise a clonal population of amplicons from an individual adaptor-template-adaptor molecule.

Embodiment 42

The method of any one of Embodiments 33-41, wherein the number of the plurality of adaptor-template-adaptor molecules exceeds the number of amplification sites, wherein the adaptor-template-adaptor molecules have fluidic access to the amplification sites, and wherein each of the amplification sites comprises a capacity for several adaptor-template-adaptor molecules.

Embodiment 43

The method of any one of Embodiments 33-42, wherein the contacting comprises simultaneously (i) transporting the adaptor-template-adaptor molecules to the amplification sites at an average transport rate, and (ii) amplifying the adaptor-template-adaptor molecules that are at the amplification sites at an average amplification rate, wherein the average amplification rate exceeds the average transport rate.

Embodiment 44

A composition comprising the adaptor-template-adaptor molecules of Embodiment 1, wherein the universal adaptor comprises a restriction endonuclease recognition site.

Embodiment 45

The composition of Embodiment 44 wherein the restriction endonuclease is SapI, MlyI, or BpuEI.

Embodiment 46

A composition comprising the plurality of reDNAs generated by the method of Embodiment 1, further comprising an artificial biological fluid.

Embodiment 47

The composition of Embodiment 46, wherein the artificial biological fluid comprises an artificial plasma.

Embodiment 48

The method of any one of Embodiments 1-32 wherein the subject is suspected of having a bacterial or viral infection.

Embodiment 49

The method of any one of Embodiments 1-32 or 48 wherein the sample comprises viral DNA or bacterial DNA.

Embodiment 50

The method of any one of Embodiments 1-32 or 48-49 wherein the sample comprises blood, urine, sputum, or stool.

Embodiment 51

A method of using a control in a nucleic acid detection test, comprising:
  a. providing a plurality of regenerated template nucleic acids (reDNAs) using the method of Embodiment 1;
  b. performing a nucleic acid detection test on a test sample and on the reDNAs obtained in step (a);
  c. analyzing results from the nucleic acid detection test using the reDNAs as a control.

Embodiment 52

The method of Embodiment 51, wherein the nucleic acid detection test comprises sequencing.

Embodiment 53

The method of any of Embodiments 51-52, wherein the nucleic acid detection test comprises microarray analysis.

Embodiment 54

The method of any of Embodiments 51-53, wherein the nucleic acid detection test comprises an enzymatic process.

Embodiment 55

A method comprising performing a nucleic acid detection test on a plurality of regenerated template nucleic acids (reDNAs) obtained using the method of Embodiment 1.

Embodiment 56

The method of Embodiment 55, wherein the reDNAs are a control for quality of library preparation methods.

Embodiment 57

The method of any of Embodiments 55-56, wherein the reDNAs are a calibration control for a sequencing instrument.

Embodiment 58

The method of any of Embodiments 55-57, wherein the reDNAs are a calibration control for an array instrument.

Embodiment 59

The method of any of Embodiments 55-58, wherein the reDNAs are a validation control for a nucleic acid sequencing test.

Embodiment 60

The method of any of Embodiments 55-59, wherein the reDNAs are a validation control for a sequencing-based noninvasive prenatal test.

Embodiment 61

The method of any of Embodiments 55-60, wherein the reDNAs are a validation control for a sequencing-based tumor detection test.

Embodiment 62

The method of any of Embodiments 55-61, wherein the reDNAs are a validation control for a sequencing-based companion diagnostic test.

Embodiment 63

The method of any of Embodiments 55-62, wherein the companion diagnostic test determines the presence or identity of genetic variants in a sample in order to determine whether a therapeutic treatment will be suitable in a treatment regimen.

EXAMPLES

The present disclosure is illustrated by the following examples. It is to be understood that the particular examples, materials, amounts, and procedures are to be interpreted broadly in accordance with the scope and spirit of the disclosure as set forth herein.

Example 1

Purpose

This example describes the creation of a Plasma Control Material that can be used in experiments as an alternative to using Human plasma. As described herein, the cfDNA input that is isolated and purified during this process (reDNA) is concentrated enough to supply dozens of plates worth of material, providing a large stock of genetically similar cfDNA which can be used over a long period of time. Additionally, the user can spike this prepared sample of DNA into a plasma diluent, creating a quantitatively similar alternative to Human blood plasma. This alternative plasma diluent can be used to mimic the qualities of Human blood plasma in experiments where cfDNA is needed, reserving the Human blood plasma for more important experiments where it is necessary.

Table 1 defines terminology used in this example.

TABLE 1

| Definitions | |
|---|---|
| Term | Definition |
| cfDNA | Cell-free DNA |
| reDNA | Regenerative DNA, an output of this protocol |
| deDNA | Deactivated DNA, an output of this protocol |

Materials & Equipment

This workflow was designed for use with cfDNA (cell-free DNA) extracted from human plasma. cfDNA was expected to have a median size of 160-170 bp.

The equipment used is described in Table 2. References and standard protocols used are described in Table 3. Reagents used are described in Table 4. Primers used are described in Table 5.

TABLE 2

| Equipment. | | |
|---|---|---|
| Equipment | Manufacturer | Model/Catalog no. |
| Liquid Handling Workstation | Hamilton | MicroLab STAR |
| Thermocycler | Bio-Rad | C1000 |
| Microplate Reader | Molecular Devices | Spectramax M2 |
| Fragment Analyzer | Agilent | BioAnalyzer |
| Qubit Reader | Invitrogen | Q32866 |

TABLE 3

| References and standard protocols. | |
|---|---|
| Reference | Part Number |
| Brigid Automated cfDNA Extraction | 1000000022985 |
| Brigid Automated Library Preparation | 1000000023194 |
| Brigid Automated DNA Quantitation | 1000000023192 |
| Brigid Automated Pooling | 1000000023196 |
| Brigid DNA Sequencing | 1000000023201 |
| Qubit 2.0 Fluorometer Manual | Thermo: MP32866 |
| 2100 Expert User's Guide | Agilent: G2946-90004 |
| Agilent DNA 1000 Kit Guide | Agilent: G2938-90014 |
| Agilent High Sensitivity DNA Kit Guide | Agilent: G2938-90321 |

TABLE 4

| Reagents | | |
|---|---|---|
| Reagent | Supplier | Part No. |
| HT1 | Illumina | 15067739 |
| Sample Purification Beads | Illumina or Beckman Coulter | 15068697 or A63882 |
| SapI Enzyme | Biolabs | |
| Elution Buffer (BE) | Macherey-Nagel | 740306.100 |
| Dynabeads MyOne Streptavidin T1 | Invitrogen | |
| Qubit dsDNA HS Assay Kit | Invitrogen | Q32851 (100 assay) Q32854 (500 Assay) |
| Agilent BioAnalyzer Reagents | Agilent | 5067-1504 (DNA 1000) 5067-4626 (DNA HS) |
| Custom Y-Adaptors | IDT | Table 5.2 |
| Biotynalated P5 and P7 Primers | IDT | Table 5.2 |
| Artificial 170 bp Sequence | IDT | Table 5.2 |
| Deactivated DNA Primers | IDT | Table 5.2 |

TABLE 5

Custom IDT Primers

| Product | | Sequences 5' → 3' | Processing |
|---|---|---|---|
| BpuEI[1] + SapI[2] Y-Adaptor | Forward | AATGATACGGCGACCACCGACTTGAG GTCGGATAGCTCTTC*T (SEQ ID NO: 1) | PAGE Purification Duplex Annealing |
| | Reverse | /5Phos/GAAGAGCTATCCGACCTCAAGA TCTCGTATGCCGTCTTCTGCTTG (SEQ ID NO: 2) | |
| Artificial 170 bp | Forward | GTCGGATAGCGCCACTATGAGCATATTCGGTT TACCTCAGATTGTATAATTGATGACGATAAAC ATTCACCGGAGAAGATCTAACGTAAGTATAT AGTTATAACTGAACCGTTCGAACACTTACTCC GTTTACTTAATTACGCCTTACTGTCATGCCTG GCTCGTAAGTT (SEQ ID NO: 3) | PAGE Purification Ultramer Synthesis |
| | Reverse | AACTTACGAGCCAGGCATGACAGTAAGGCGT AATTAAGTAAACGGAGTAAGTGTTCGAACGG TTCAGTTATAACTATATACTTACGTTAGATCTT CTCCGGTGAATGTTTATCGTCATCAATTATAC AATCTGAGGTAAACCGAATATGCTCATAGTG GCGCTATCCGAC (SEQ ID NO: 4) | |
| Deactivated DNA Primers | Forward | /5InvddT/AACTTACGAGCCAGGCATGACAGTA (SEQ ID NO: 5) | PAGE Purification |
| | Reverse | /5InvddT/GTCGGATAGCGCCACTATGAGCATA (SEQ ID NO: 6) | |

[1]The nucleotides corresponding to the BpuEI site are underlined
[2]The nucleotides corresponding to the SapI site are underlined and italicized.

Amplification of Template DNA
Reagent Preparation and Handling

The library was prepared as described (U.S. Pat. No. 9,323,888), but the VeriSeq NIPT adaptor plate was replaced with the custom Y-adaptors, and the plate was eluted with PCR mix.

SapI adaptors were diluted 1:100 in Dilution Buffer according to Table 6, and mixed for 10 seconds using a vortex mixer. Custom Adaptor Mix (30 uL) were transferred to an Eppendorf Skirted Twin-Tec 96 well Plate.

TABLE 6

Reagent Dilution for Custom Adaptor Mix, 48 Batch

| Batch Size | Adaptor Stock 18 nM (uL) | Dilution Buffer (uL) |
|---|---|---|
| 48 Samples | 15 | 1485 |
| 96 Samples | 30 | 2970 |

SPRI beads were removed from 4° C. storage, placed on rotisserie, and rotated at room temperature for approximately 30 minutes. The 96-well full-skirt cfDNA sample plate was removed from either 4° C. or −20° C. storage, thawed completely if necessary, mixed using a vortex mixer for 20 seconds, and centrifuged at 1000 g for 20 seconds.

The PCR mix was prepared for bead elution using enhanced PCR mix, biotinylated primer, and resuspension buffer.

The reagents for an Invitrogen Qubit DNA 1000 Assay Kit were thawed.

Modified VeriSeq NIPT 48 Library

The Hamilton Star Run Control was opened and the Veriseq NIPT Method (version 1.4 or later) was run using the manufacturer instructions. After the liquid detection check, 20 mL reservoir containing Elution Buffer or HT1 at position 5 of the carrier on track 47 was removed.

After the bead drying step and before the method plates out HT1 or Elution Buffer, the SPRI bead plate at position 5 of the 3×2 multiflex carrier found on tracks 19-24 was removed. Alternatively, the method can be allowed to finish, as the Hamilton will not plate out the HT1 or Elution buffer if the 20 mL reservoir containing the reagents was removed.

To elute the beads with 50 uL of PCR mix per well, the plate was covered with a foil seal, mixed by vortex, spun down on a centrifuge, and placed on a plate magnet for a minimum of 2 minutes and until the solution was clear. The supernatant (50 uL) was transferred to an Eppendorf full-skirt Twin-tec 96 well plate.

PCR Amplification

The sample plate was placed on the thermocycler and the EPM14 program selected. The EPM 14 program is outlined in Table 7. After completion of the EPM14 the plate was removed from the thermocycler. If there were no additional cycles of PCR, then proceed to the next section: "Streptavidin Binding, Digestion, and Purification."

TABLE 7

EPM 14 Program

| Steps | Temperature | Time |
|---|---|---|
| Denaturation | 95° C. | 3:00 mins |
| Amplification | | 14 Cycles x |
| | 98° C. | 20 sec |
| | 60° C. | 15 sec |
| | 72° C. | 30 sec |
| Final Extension | 72° C. | 5:00 mins |
| Hold | 10° C. | forever |

Quantification and Dilution (for Second PCR Only)

PCR Product (50 μL) was combined with 9504, Resuspension Buffer (RB) in a 1.5 mL or 2 mL tube for a 1:20 dilution totaling 1 ml. The solution was mixed using a vortex mixer and spun down.

The Qubit Reader was used as recommended by the manufacturer. Qubit readings were performed using 2 separate tubes with 10 μL sample input per sample and averaging the resulting readings. After diluting to 60 pg/μL, the desired volume of 1:20 EPM 14 product was combined in a volume appropriate tube (5 mL, 15 mL, or 50 mL polypropylene tube) with the indicated volume of Resuspension Buffer. The final dilution was mixed and spun down, and the remaining 1:20 dilution stock was retained at −20° C. for future use.

Second PCR Amplification

EPM 14 Product (25 uL of 60 pg/μL) was added in a new 96 well plate. PCR Mix (25 uL) was added to this solution for a total volume of 50 uL, and mixed. The plate was placed on the thermocycler and the EPM 13 Program, outlined in Table 8, was selected.

TABLE 8

EPM 13 Program

| Steps | Temperature | Time |
|---|---|---|
| Denaturation | 95° C. | 3:00 mins |
| Amplification | | 13 Cycles x |
| | 98° C. | 20 sec |
| | 60° C. | 15 sec |
| | 72° C. | 30 sec |
| Final Extension | 72° C. | 5:00 mins |
| Hold | 10° C. | forever |

After the PCR was done the plate was removed from the thermocycler. Sample replicates were pooled in appropriately sized tubes (5 mL, 15 mL, or 50 mL polypropylene), and the Bioanalyzer DNA 1000 chip was run to verify PCR amplification. Five microliters of sample was diluted with 15 μL of Resuspension Buffer to create a 1:4 dilution before running on the bioanalyzer. The peak size for amplified library centered close to 260-270 bp.

Output and Storage

The plate can be sealed and stored at 2° C. to 8° C. for use later the same day, or sealed and stored at −20° C. to −15° C. or storage overnight or longer.

Streptavidin Binding, Digestion, and Purification

Reagent Prep and Handling

Dynabeads MyOne Streptavidin T1 was placed on a rotisserie for up to 30 minutes at room temperature. Reactions may take place in a deep-well plate or a volume appropriate polypropylene tube. For each digestion reaction, follow Table 9 to create sufficient digestion mix. Multiply volumes by total reactions needed to make sufficient mix. Keep the SapI Digestion mix on ice or at 4° C. until needed. Incubate DNA 1000 bioanalyzer reagents for at least 30 mins in the dark at room temperature.

TABLE 9

Volume breakdown for each SapI Digestion

| Reaction Size | Nuclease-Free Water | Cutsmart Buffer | SapI Enzyme | Total Volume |
|---|---|---|---|---|
| Small (1 PCR Reaction) | 328 μL | 40 μL | 32 μL | 400 μL |

TABLE 9-continued

Volume breakdown for each SapI Digestion

| Reaction Size | Nuclease-Free Water | Cutsmart Buffer | SapI Enzyme | Total Volume |
|---|---|---|---|---|
| Large (7.5 PCR Reactions) | 2460 μL | 300 μL | 240 μL | 3000 μL |

Streptavidin Bead Wash

For each sample to be digested, the volume of streptavidin beads from Table 10 was dispensed into the reaction vessel.

TABLE 10

Digestion Reaction and Deactivation Volume:

| Reaction Size | Streptavidin Beads | PCR Amplified DNA | SapI Digestion | 5 mM EDTA |
|---|---|---|---|---|
| Small (1 PCR Reaction) | 200 μL | 50 μL | 400 μL | 4 μL |
| Large (7.5 PCR Reactions) | 1500 μL | 375 μL | 3000 μL | 30 μL |

An equal volume of 1× Bead Wash was added to each tube with streptavidin beads and mixed. The 1× Bead Wash was equal volume distilled water and MyONE T1 Bead Wash. MyONE T1 Bead wash can be made ahead of time and stored at 2° C. to 8° C. MyONE T1 Bead wash can be made by combining 10 mM Tris pH 7.5, 1 mM EDTA, and 2M NaCl. The mixture was placed on a magnet until the solution was clear (minimum of 1 minute). On half (½) of the supernatant was removed, and the vessel was removed from the magnet. This was repeated two additional times for a total of 3 washes. The vessel of washed beads was removed from the magnet.

Restriction Digestion

The reaction vessel with washed beads was placed on the magnet for until the solution is clear (minimum of 1 minute). All the supernatant was removed so that only the beads remained in the vessel. The volume of PCR Product indicated in Table 10 was added to dried beads and mixed to resuspend the beads. The binding mix was mixed on the Eppendorf ThermoMixer for 20 minutes at 1500 RPM and 20° C. After briefly spinning down the vessel, the vessel was placed on the magnet until the solution cleared (minimum 1 minute). All supernatant was removed while the tube was still on the magnet. The volume of digestion mix indicated in Table 10 was added to the vessel, and the vessel placed on the Eppendorf ThermoMixer for 1 hour at 1500 RPM and 37° C. After the incubation, the appropriate volume of EDTA from Table 10 was added to the reaction vessel, mixed, spun down, and the vessel was placed on magnet until the solution clears (minimum 2 minutes).

The supernatant sample (now referred to as reDNA) was carefully transferred to a new volume appropriate polypropylene vessel. The purified sample pool (5 μL of sample diluted with 5 μL of Resuspension Buffer to create a 1:2 before running) was run on a Bioanalyzer DNA High-Sense chip to confirm digestion. The peak size for cfDNA centered close to 165-170 bp. Samples with abnormal Bioanalyzer profiles were retest and/or discarded. Digestions of the same sample that met QC requirements were pooled into a volume appropriate polypropylene tube. The samples were stored at −20° C. for long term storage.

Creation of Control Material
Reagent Prep and Handling

After thawing, an aliquot of 1:2 sample dilution of reDNA samples was created by combining 10 μL of reDNA with 10 μL of Resuspension Buffer. A 1:200 dilution of dye was created using Qubit reagent and Qubit buffer.

Creation of Deactivated DNA (deDNA)

Deactivated DNA (deDNA) is amplified DNA from a non-human 170 bp sequence with 5' inverted ddt modifications that prevent any enzymatic activity (including ligation).

A primer mix for the inverted ddt PCR Primer Cocktail was made by combining 300 uL Elution Buffer and 50 uL of each reverse and forward Primers (for a total of 100 uL). The template DNA was diluted to 50 pg/uL. Template can be either previously amplified deDNA or freshly ordered artificial 170 bp. Twenty five microliters of substrate DNA was combined with 25 uL of the inverted ddt PCR Primer Cocktail, placed on a thermocycler, and run using EPM 14. After completion all reactions were pooled. The deDNA can be stored at −20° C.

Qubit Quantitation

Qubit readings were performed with the 1:2 sample dilution using 2 separate tubes per reDNA and deDNA sample, one tube with 10 μL (High) sample input and one tube with 5 μL (Low) input.

The final concentrations were determined by multiplying the Qubit measurement (ng/mL) of High Concentration tubes by 40 and the Qubit measurement (ng/mL) of Low Concentration tubes by 80. If the difference between High and Low readings was greater than 30% of the lower of the two concentration readings, Qubit quantitation was re-performed. the High and Low readings final concentrations was averaged as the final concentration (now in pg/μL). Qubit quantitation was performed any time the reDNA stock was thawed from −20° C. storage.

Creating Artificial Plasma

Each 900 μL artificial plasma produced contained 50% Plasma Diluent (ImmunoChemistry Technologies, Bloomington, MNac), 2 mM EDTA, 3.5 ng reDNA, 3.5 ng deDNA, and dPBS to fill.

In a volume appropriate polypropylene vessel the appropriate volume of plasma diluent was added and mixed use a stir-bar if substantial volumes were created. In a volume appropriate vessel the total required dPBS was measured out. In two volume appropriate polypropylene vessels (at least 4× deDNA and reDNA volumes): the vessel was filled to 50% with dPBS from the measured reserve, the appropriate volume of reDNA and deDNA was added (one per tube), the appropriate volume of EDTA to was added the reDNA tube, the remaining dPBS from reserve was added into the mix vessel with the plasma diluent, and mixed using a stir-bar or inversion. The deDNA and reDNA tubes were sealed and vigorously vortex mixed. The deDNA tube contents were added to the mix vessel and mixed for 5 minutes, and then the reDNA tube contents were added to the mix vessel and mixed for a minimum of 30 minutes.

The artificial Plasma can be aliquoted into screw top tubes for long term storage at −80° C. freezer, until used as normal human maternal plasma.

Example 2

Characterization of reDNA

The purpose of this test was to compare metrics of a noninvasive prenatal test performed on either reDNA or the corresponding cfDNA from which the reDNA fragments were derived. reDNA was generated as described in Example 1 from cfDNA extracted from plasma derived from whole blood obtained from healthy pregnancies. The blood was obtained from 48 pregnancies including a mixture of healthy male and female fetuses. Blood was obtained from patients under proper consent.

A sequencing-based noninvasive prenatal test was performed on original cfDNA, and on the reDNA derived from the cfDNA. The test was performed as described in U.S. Pat. No. 10,095,831, the contents of which are incorporated herein by reference in its entirety. Sequencing metrics and other NIPT test metrics from the test included fetal fraction based on fragment size and/or coverage, NIPT test results statistics including t-statistic and log likelihood ratio (LLR).

The primary NIPT metrics, summarized in the table below, indicate that reDNA was consistently and proportionally equivalent to the matched plasma sample. Any bias in the reDNA was reproducible and consistent. For example, relationships between short and long reads in ChrX were maintained in plasma and reDNA samples. The results indicate that reDNA can be useful as a control for NIPT test validation.

TABLE 10

NIPT metrics.

| Metric | Result from 48-plex |
|---|---|
| FF Size | no bias |
| FF_Coverage | no bias |
| FF_Cov_Size | no bias |
| FF_XY | prop bias 9.2% |
| FF_X | prop bias 7.4% |
| FF_Y | prop bias 10% |
| Bin_MAD | prop. bias 20% |
| FragSizeDist | constant shift |
| Tags2IR | noisy, but no constant bias |
| ERC2Tags | linear bias |
| GCBias_Slope | variable |
| LLR | linear bias (0.74 slope) |
| Tstat numerator | prop. Bias 6.5% |
| TstatSD | linear bias (0.52 slope) |

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The disclosure is not limited to the exact details shown and described, for variations obvious to one skilled in the art will be included within the disclosure defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present disclosure. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method of using a control in a nucleic acid detection test, the method comprising:
   providing a plurality of double-stranded template nucleic acids originating from a sample obtained from a subject, wherein the double-stranded template nucleic acids comprise a population of sizes and sequences similar to or identical to the sizes and sequences obtained from the subject;
   ligating a universal adapter to both ends and both strands of the template nucleic acids to form a plurality of adapter-template-adapter molecules comprising template nucleic acids flanked by the universal adapter, wherein the universal adapter comprises a region of double stranded nucleic acid; and
   amplifying the plurality of adapter-template-adapter molecules with a first universal primer and a second universal primer to result in amplified adapter-template-adapter molecules;
   removing at least a portion of the universal adapter from both ends of the amplified adapter-template-adapter molecules to result in removed universal adapters and a plurality of regenerated template nucleic acids (reDNAs), wherein the reDNAs comprise a population of template molecules of sizes and sequences similar to or identical to the sizes and sequences obtained from the subject;
   performing a nucleic acid detection test on a test sample and on the reDNAs; and
   analyzing results from the nucleic acid detection test using the reDNAs as a synthetic control.

2. The method of claim 1 wherein the double-stranded template nucleic acids comprise cell free DNA (cfDNA).

3. The method of claim 1 wherein the subject is a pregnant human, and wherein the double-stranded template nucleic acids comprise a mixture of fetal and maternal nucleic acids.

4. The method of claim 3 wherein the sample comprises cfDNA.

5. The method of claim 3 wherein the fetus comprises a genetic condition.

6. The method of claim 5 wherein the genetic condition is an aneuploidy.

7. The method of claim 1 wherein the subject is suspected of having a neoplasm.

8. The method of claim 7 wherein the sample comprises circulating tumor DNA and cell free normal DNA.

9. The method of claim 1 wherein the universal adapter comprises a restriction endonuclease recognition site, and the removing comprises exposing the amplified adapter-template-adapter molecules to a restriction endonuclease and cleaving the adapter-template-adapter molecules to result in removed universal adapters and a plurality of reDNAs.

10. The method of claim 9 wherein the cleavage site and the recognition site of the restriction endonuclease are separate.

11. A method of using a control in a nucleic acid detection test, the method comprising:
   providing a plurality of regenerated template nucleic acids (reDNAs) originating from a sample obtained from a subject, wherein the reDNAs comprise a population of template molecules of sizes and sequences similar to or identical to the sizes and sequences obtained from the subject,
   wherein each reDNA is an amplified template;
   ligating a universal adapter to both ends of the template nucleic acids to form a plurality of adapter-template-adapter molecules comprising a template nucleic acid flanked by the universal adapter,
   wherein the universal adapter comprises (i) a region of double stranded nucleic acid, and (ii) a region of single-stranded non-complementary nucleic acid strands comprising at least one universal primer binding site,
   thereby producing a sequencing library for determining the sequence of at least a portion of templates
   performing a nucleic acid detection test on a test sample and on the sequencing library; and
   analyzing results from the nucleic acid detection test using the at least a portion of the sequencing library as a synthetic control.

12. The method of claim 11, further comprising:
   providing a surface comprising a plurality of amplification sites,
   wherein the amplification sites comprise at least two populations of attached single stranded nuclei acids having a free 3' end, and
   contacting the surface comprising amplification sites with the plurality of adapter-template-adapter molecules under conditions suitable to produce a plurality of amplification sites that each comprise a clonal population of amplicons from an individual adapter-template-adapter molecule.

13. A method comprising performing a nucleic acid detection test on a plurality of regenerated template nucleic acids (reDNAs) obtained using the method of claim 1.

14. The method of claim 13, wherein the reDNAs are a control for quality of library preparation methods.

15. The method of claim 13, wherein the reDNAs are a calibration control for a sequencing instrument.

16. The method of claim 13, wherein the reDNAs are a validation control for a nucleic acid sequencing test.

17. A method of using a control in a nucleic acid detection test, the method comprising:
- providing a plurality of double-stranded template nucleic acids originating from a sample obtained from a subject, wherein the subject is a pregnant human, wherein the double-stranded template nucleic acids comprise a mixture of fetal and maternal nucleic acids, and wherein the double-stranded template nucleic acids comprise a population of sizes and sequences similar to or identical to the sizes and sequences obtained from the subject;
- ligating a universal adaptor to both ends of the template nucleic acids to form a plurality of adaptor-template-adaptor molecules comprising a template nucleic acid flanked by the universal adaptor, wherein the universal adaptor comprises a region of double stranded nucleic acid; and
- amplifying, such as by an exponential amplification reaction, the plurality of adaptor-template-adaptor molecules with a first universal primer and a second universal primer to result in amplified adaptor-template-adaptor molecules;
- removing at least a portion of the universal adaptor from both ends of the amplified adaptor-template-adaptor molecules to result in removed universal adaptors and a plurality of regenerated template nucleic acids (reDNAs), wherein the reDNAs comprise a population of template molecules of sizes and sequences similar to or identical to the sizes and sequences obtained from the subject;
- performing a nucleic acid detection test on a test sample and on the reDNAs; and
- analyzing results from the nucleic acid detection test using the reDNAs as a synthetic control.

18. The method of claim 17, wherein the amplification reaction is a polymerase chain reaction (PCR).

19. The method of claim 1, wherein the test sample is from a different subject.

* * * * *

SEQUENCE LISTING

```
<160> NUMBER OF SEQ ID NOS: 6

<210> SEQ ID NO 1
<211> LENGTH: 42
<212> TYPE: DNA
<213> ORGANISM: Artificial Sequence
<220> FEATURE:
<223> OTHER INFORMATION: Synthetic primer

<400> SEQUENCE: 1
aatgatacgg cgaccaccga cttgaggtcg gatagctctt ct                          42

<210> SEQ ID NO 2
<211> LENGTH: 45
<212> TYPE: DNA
<213> ORGANISM: Artificial Sequence
<220> FEATURE:
<223> OTHER INFORMATION: Synthetic primer

<400> SEQUENCE: 2
gaagagctat ccgacctcaa gatctcgtat gccgtcttct gcttg                       45

<210> SEQ ID NO 3
<211> LENGTH: 170
<212> TYPE: DNA
<213> ORGANISM: Artificial Sequence
<220> FEATURE:
<223> OTHER INFORMATION: Synthetic primer

<400> SEQUENCE: 3
gtcggatagc gccactatga gcatattcgg tttacctcag attgtataat tgatgacgat       60
aaacattcac cggagaagat ctaacgtaag tatatagtta taactgaacc gttcgaacac      120
ttactccgtt tacttaatta cgccttactg tcatgcctgg ctcgtaagtt                 170

<210> SEQ ID NO 4
<211> LENGTH: 170
<212> TYPE: DNA
<213> ORGANISM: Artificial Sequence
<220> FEATURE:
<223> OTHER INFORMATION: Synthetic primer

<400> SEQUENCE: 4
aacttacgag ccaggcatga cagtaaggcg taattaagta aacggagtaa gtgttcgaac       60
ggttcagtta taactatata cttacgttag atcttctccg gtgaatgttt atcgtcatca     120
attatacaat ctgaggtaaa ccgaatatgc tcatagtggc gctatccgac                 170

<210> SEQ ID NO 5
<211> LENGTH: 26
<212> TYPE: DNA
<213> ORGANISM: Artificial Sequence
<220> FEATURE:
<223> OTHER INFORMATION: Synthetic primer
```

-continued

```
<400> SEQUENCE: 5
taacttacga gccaggcatg acagta                                              26

<210> SEQ ID NO 6
<211> LENGTH: 26
<212> TYPE: DNA
<213> ORGANISM: Artificial Sequence
<220> FEATURE:
<223> OTHER INFORMATION: Synthetic primer

<400> SEQUENCE: 6
tgtcggatag cgccactatg agcata                                              26
```